(12) United States Patent
Roberts et al.

(10) Patent No.: US 7,230,089 B1
(45) Date of Patent: Jun. 12, 2007

(54) METHODS FOR INCREASING PLANT CELL PROLIFERATION BY FUNCTIONALLY INHIBITING A PLANT CYCLIN INHIBITOR GENE

(75) Inventors: James M. Roberts, Seattle, WA (US); Beth L. Kelly, San Francisco, CA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 09/980,758

(22) PCT Filed: May 15, 2000

(86) PCT No.: PCT/US00/13379

§ 371 (c)(1), (2), (4) Date: Feb. 19, 2003

(87) PCT Pub. No.: WO00/69883

PCT Pub. Date: Nov. 23, 2000

Related U.S. Application Data

(60) Provisional application No. 60/134,373, filed on May 14, 1999.

(51) Int. Cl.
*C12N 15/29* (2006.01)
*C12N 15/82* (2006.01)

(52) U.S. Cl. ............... 536/23.6; 435/320.1; 435/252.3

(58) Field of Classification Search ............. 536/23.6; 435/320.1, 252.3
See application file for complete search history.

(56) References Cited

U.S. PATENT DOCUMENTS

| | | | |
|---|---|---|---|
| 5,283,173 | A | 2/1994 | Fields et al. |
| 5,583,210 | A | 12/1996 | Neill et al. |
| 5,688,665 | A | 11/1997 | Massague et al. |
| 5,750,862 | A | 5/1998 | John |

FOREIGN PATENT DOCUMENTS

| | | |
|---|---|---|
| WO | 99/14331 | 3/1999 |
| WO | 99/64599 | 12/1999 |

OTHER PUBLICATIONS

Luban J. et al. The yeast two-hybrid system for studying protein-protein interactions. Curr Opin Biotechnol. Feb. 1995;6(1):59-64. Review.*

Caponigro G. et al. Functional analysis of expressed peptides that bind yeast STE proteins. J Biotechnol. Aug. 15, 2003;103(3):213-25.*

Whisstock J.C. et al. Prediction of protein function from protein sequence and structure. Q Rev Biophys. Aug. 2003;36(3):307-40. Review.*

Zhou Y. et al. The plant cyclin-dependent kinase inhibitor ICK1 has distinct functional domains for in vivo kinase inhibition, protein instability and nuclear localization. Plant J. Aug. 2003;35(4):476-89.*

EMBL Acession No. Q9LJL5, Cyclin-dependent kinase inhibitor 6 from Arabidopsis thaliana (Name=ACK1; Synonyms=krp6), Oct. 1, 2000, Nakamura Y.*

Bai and Elledge, "Gene identification using the yeast two-hybrid System," *Methods in Enzymology* 273:331-347 (1996).

Bartel et al., "Using the two-hybrid system to detect protein-protein interactions," in *Cellular Interaction in Development: A Practical Approach*, Ed. Hartley, Oxford University Press, Oxford, ENGLAND, pp. 153-179 (1993).

Bechtold and Pelletier, "*In planta agrobacterium*-mediated transformation of adult *Arabidopsis thaliana* plants by vacuum infiltration," *Methods Mol. Biol.* 82:259-266 (1998).

Chen et al., "*LEUNIG* has multiple functions in gynoecium development in *arabidopsis*," *Genesis* 26:42-54 (2000).

Clark et al., "The *CLAVATA* and *SHOOT MERISTEMLESS* loci competitvely regulate meristem activity in *arabidopsis*," *Development* 122:1567-1575 (1996).

Coats et al., "Requirement of $p27^{Kip1}$ for restriction point control of the fibroblast cell cycle," *Science* 272:877-880 (1996).

Comai et al., "Novel and useful properties of a chimeric plant promoter combining CaMV 35S and MAS elements," *Plant Mol. Biol.* 15:373-381 (1990).

Day and Reddy, "Isolation and characterization of two cyclin-like cDNAs from *Arabidopsis*," *Plant Mol. Biol.* 36:451-461 (1998).

Doerner et al., "Control of root growth and development by cyclin expressions," *Nature* 380:520-523 (1996).

Doonan and Fobert, "Conserved and novel regulators of the plant cell cycle," *Curr. Opin. Cell Biol.* 9:824-830 (1997).

Durfee et al., "The retinoblastoma protein associates with the protein phosphatase type 1 catalytic subunit," *Genes & Devel.* 7:555-569 (1993).

(Continued)

*Primary Examiner*—Cynthia Collins
(74) *Attorney, Agent, or Firm*—Townsend and Townsend and Crew LLP

(57) ABSTRACT

The present invention provides methods for modulating the growth and/or yield of plants. In particular the methods comprise the use of agents which functionally inhibit the expression of plant D-like cyclin inhibitors including isolated polynucleotide sequences which interact with DNA or RNA encoding proteins capable of binding plant D-like cyclins. Further, the present invention provides recombinant polynucleotide sequences, vectors and host cells which encode proteins capable of binding to and inactivating the activity of plant D-like cyclin/cyclin dependent kinase complexes preventing plant cells from exiting the cell cycle. Methods for determining and agents which are inhibitors of the BRO cyclin dependent kinase inhibitor proteins which are capable of modulating plant cell cycle progression are also provided. Methods for the production of transgenic plant cells and plants with increased growth rates and yields when compared to wild-type plants are also provided.

10 Claims, 2 Drawing Sheets

OTHER PUBLICATIONS

El-Deiry et al., "*WAF1*, a potential mediator of p53 tumor suppression," *Cell* 75:817-825 (1993).

Feiler et al., "Cell division in higher plants: A *cdc2* gene, its 34-jDa product, and histone H1 kinase activity in pea," *Proc. Natl. Acad. Sci USA* 87:5397-5401 (1990).

Ferreira et al., "The *Arabidopsis* functional homolog of the $p34^{cdc2}$ protein kinase," *Plant Cell* 3:531-540 (1991).

Fields and Sternglanz, "The two-hybrid system: an assay for protein-protein interactions," *Trends in Genetics* 10:286-292 (1994).

Fields and Song, "A novel genetic system to detect protein-protein interactions," *Nature* 340:245-246 (1989).

Fletcher et al., "Signaling of cell fate decisions by *CLAVATA3* in *Arabidopsis* shoot meristems," *Science* 283:1911-1914 (1999).

Fotedar et al., "p21 contains independent binding sites for cyclin and cdk2: both sites are required to inhibit cdk2 kinase activity," *Oncogene* 12(10):2155-2164 (1996).

Gould et al., "Studies on control of the cell cycle in cultured plant cells, I. effects of nutrient limitation and nutrient starvation," *Protoplasma* 106:1-13 (1981).

Gould et al., "Phosphorylation at Thr167 is required for *Schizosaccharomyces pombe* $p34^{cdc2}$ function," *EMBO J.* 10:3297-3309 (1991).

Hannon and Beach, "$p15^{INK4B}$ is a potential effector of TGF-β-induced cell cycle arrest," *Nature* 371:257-261 (1994).

Harper et al., "The p21 Cdk-interacting protein Cip1 is a potent inhibitor of G1 cyclin-dependent kinases," *Cell* 75:805-816 (1993).

Hata et al., "Isolation and characterization of cDNA clones for plant cyclins," *EMBO J.* 10:2681-2688 (1991).

Hemerly et al., "Genes regulating the plant cell cycle: isolation of a mitotic-like cyclin from *Arabidopsis thaliana*," *Proc. Natl. Acad. Sci. USA* 89:3295-3299 (1992).

Hirayama et al., "Identification of two cell-cycle controlling *cdc2* gene homologs in *Arabidopsis thaliana*," *Gene* 105:159-165 (1991).

Hirt et al., "Complementation of a yeast cell cycle mutant by an alfalfa cDNA encoding a protein kinase homologous to $p34^{cdc2}$," *Proc. Natl. Acad. Sci USA* 88:1636-1640 (1991).

Hirt et al., "*cdcMsB*, a cognate *cdc2* gene from alfalfa, complements the G1/S but not the G2/M transition of budding yeast *cdc28* mutants," *Plant J.* 4:61-69 (1993).

Hollenberg et al., "Identification of a new family of tissue-specific basic helix-loop helix proteins with a two-hybrid system," *Mol. Cell. Biol.* 15:3813-3822 (1995).

Hsieh et al., "Isolation and characterization of a functional A-type cyclin from maize," *Plant Mol. Biol.* 37:121-129 (1998).

Huntley et al., "The maize retinoblastoma protein homologue ZmRb-1 is regulated during leaf development and displays conserved interactions with G1/S regulators and plant cyclin D (CycD) proteins," *Plant Mol. Biol* 37:155-169 (1998).

Ito et al., "A novel *cis*-acting element in promoters of plant B-type cyclin genes activates M phase-specific transcription," *Plant Cell* 10:331-341 (1998).

Jeffrey et al., "Mechanism of CDK activation revealed by the structure of a cyclinA-CDK2 complex," *Nature* 376:313-320 (1995).

John, "The plant cell cycle: conserved and unique features in mitotic control," *Prog. Cell Cycle Res.* 2:59-72 (1996).

Kato et al., "Cyclic AMP-induced G1 phase arrest mediated by an inhibitor ($P27^{Kip1}$) of cyclin-dependent kinase 4 activation," *Cell* 79:487-496 (1994).

Kim et al., "Protein-protein interactions among the Aux/IAA proteins," *Proc. Natl. Acad. Sci. USA* 94:11786-11791 (1997).

Koff et al., "Negative regulation of G1 in mammalian cells: inhibition of cyclin E-dependent kinase by TGF-β," *Science* 260:536-539 (1993).

Larsson et al., "Cell cycle regulation of human diploid fibroblasts: possible mechanisms of platelet-derived growth factor," *J. Cell. Phys.* 139:477-483 (1989).

Lee et al., "Cloning of $p57^{KIP2}$, a cyclin-dependent kinase inhibitor with unique domain structure and tissue distribution," *Genes Dev.* 9:639-649 (1995).

Matsuoka et al., "$p57^{KIP2}$, a structurally distinct member of the $p21^{CIP1}$ Cdk inhibitor family, is a candidate tumor suppressor gene," *Genes Dev.* 9:650-662 (1995).

McBride and Summerfelt, "Improved binary vectors for *Agrobacterium*-mediated plant transformation," *Plant Mol. Biol.* 14:269-276 (1990).

Mengiste et al. "Prospects for the Precise Engineering of Plant Genomes by Homologous Recombination," *Bio. Chem.* 380:749-758 (1999).

Mironov et al., "Regulation of cell division in plants: an *Arabidopsis* perspective," *Prog. Cell. Cycle Res.* 3:29-41 (1997).

Morgan, "Principles of CDK regulation," *Nature* 374:131-134 (1995).

Nourse et al., "Interleukin-2 mediated elimination of the $p27^{Kip1}$ cyclin-dependent kinase inhibitor prevented by rapamycin," *Nature* 372:570-573 (1994).

Ohtsubo and Roberts, "Cyclin-dependent regulation of $G_1$ in mammalian fibroblasts," *Science* 259:1908-1912 (1993).

Pardee, "A restriction point for control of normal animal cell proliferation," *Proc. Natl. Acad. Sci. USA* 71:1286-1290 (1974).

Pines, J. "Cyclines and cyclin-dependent kinases: a biochemical view," *Biochem J.* 308:697-711 (1995).

Polyak et al., "Cloning of $p27^{Kip1}$, a Cyclin-dependent kinase inhibitor and a potential mediator of extracellular antimitogenic signals," *Cell* 78:59-66 (1994).

Renaudin et al., "Plant cyclins: a unified nomenclature for plant A-, B-and D type cyclones based on sequence organization," *Plant Mol. Biol.* 32:1003-1018(1996).

Resnitzky and Reed, "Different roles for cyclins D1 and E in regulation of the $G_1$ -to-S transition," *Mol. Cell. Biol.* 15:3463-3469 (1995).

Rose et al., "Consensus-degenerate hybrid oligonucleotide primers for amplification of distantly-related sequences," *Nucleic Acids Res.* 26(7):1628-1635 (1998).

Serrano et al., "A new regulatory motif in cell-cycle control causing specific inhibition of cyclin D/CDK4," *Nature* 366:704-707 (1993).

Sherr, C. et al. "CDK inhibitors: positive and negative regulators of $G_1$ -phase progression," *Genes Develop.* 13:1501-1512 (1999).

Sherr, "G1 Phase Progression: cycling on Cue," *Cell* 79:551-555 (1994).

Slingerland et al., "A novel inhibitor of cyclin-cdk activity detected in transforming growth factor β-arrested epithelial cells," *Mol. Cell. Biol.* 14:3683-3694 (1994).

Solomon et al., "CAK, the $p34^{cdc2}$ activating kinase, contains a protein identical or closely realted to $p40^{MO15}$," *EMBO J.* 12:3133-3142 (1993).

Solomon et al., "Role of phosphorylation in $p34^{cdc2}$ activation: identification of an activating kinase," *Mol. Biol. Cell* 3:13-27 (1992).

Soni et al., "A family of cyclin D homologs from plants differentially controlled by growth regulators and containing the conserved retinoblastoma protein interaction motif," *Plant Cell* 7:85-103 (1995).

Temin, "Stimulation by serum of multiplication of stationary chicken cells," *J. Cell. Phys.* 78:161-170 (1971).

Trehin et al., "Cell cycle regulation by plant grown regulators: involvement of auxin and cytokin in the re-entry of *Petunia* protoplasts into the cell cycle," *Planta* 206:215-224 (1998).

Trehin et al., "Cloning of upstream sequences responsible for cell cycle regulation of the *Nicotiana sylvestris CycB1*; 1 gene," *Plant Mol. Biol.* 35:667-672 (1997).

Toyoshima and Hunter, "p27, a novel inhibitor of G1 cyclin-cdk protein kinase activity, is related p21," *Cell* 78:67-74 (1994).

Umeda et al., "A distinct cyclin-dependent kinase-activating kinase of *Arabidopsis thaliana*," *Proc. Natl. Acad. Sci. USA* 95:5021-5026 (1998).

Valancius, et al. "Testing an "In-Out" targeting procedure for making subtle genomic modifications in mouse embryonic stem cells," *Mol. Cell. Biol.* 3:1402-1408 (1991).

Vojtek et al., "Mammalian Ras interacts directly with the serine/threonine kinase Raf," *Cell* 74:205-214 (1993).

Walker, "Receptor-like protein kinase genes of *Arabidopsis thaliana*," *Plant J.* 3:451-456 (1993).

Wang et al. "A plant cyclin-dependent kinase inhibitor gene," *Nature* 386:451-452 (1997).

Wang et al., "ICK1, a cyclin-dependent protein inhibitor from *Arabidopsis thaliana* interacts with both Cdc2a and CycD3, and its expression is induced by abscisic acid," *Plant J.* 15:501-510 (1998).

Waterhouse et al., "Virus resistance and gene silencing in plants can be induced by simultaneous expression of sense and antisense RNA," *Proc. Natl. Acad. Sci. USA* 95:13959-13964 (1998).

Xiong et al., "p21 is a universal inhibitor of cyclin kinases," *Nature* 366:701-703 (1993).

Zetterberg et al., "Kinetic analysis of regulatory events in $G_1$ leading to proliferation or quiescence of Swiss 3T3 cells," *Proc. Natl. Acad. Sci. USA* 82:5365-5369 (1985).

De Veylder et al., "Functional Analysis of Cyclin-Dependent Kinase Inhibitors of Arabidopsis," *Plant Cell* 13:1653-1667 (2001).

Fero et al., "A Syndrome of Multiogran Hyperplasia with Features of Gigantism, Tumorigenesis, and Female Sterility in $p27^{Kip1}$-Deficient Mice," *Cell* 85:733-744 (1996).

Mironov et al., "Cyclin-Dependent Kinases and Cell Division in Plants: the Nexus," *Plant Cell* 11:509-521 (1999).

Wang et al., "ICK1, A Cyclin-Dependent Protein Kinase Inhibitor From *Arabidopsis Thaliana* Interacts with Both Cdc2a And CycD3, and its Expression is Induced by Abscisic Acid," *Plant* 15:501-510 (1998).

Y. Zhou et al., "Plant CDK Inhibitors: Studies of Interactions with Cell Cycle Regulators in the Yeast Two-Hybrid System and Functional Comparisons in Transgenic *Arabidopsis* Plants," *Plant Cell Rep.* 20:967-975 (2002).

\* cited by examiner

METHODS FOR INCREASING PLANT CELL PROLIFERATION BY FUNCTIONALLY INHIBITING A PLANT CYCLIN INHIBITOR GENE

CROSS-REFERENCES TO RELATED APPLICATIONS

This application claims priority to and benefit of U.S. Provisional application Ser. No. 60/134,373, filed May 14, 1999, the disclosure of which is incorporated herein by reference.

STATEMENT AS TO RIGHTS TO INVENTIONS MADE UNDER FEDERALLY SPONSORED RESEARCH AND DEVELOPMENT

The U.S. government may have certain rights in the invention pursuant to Grant No. R01 CA67893 received from the U.S. National Institutes of Health.

BACKGROUND OF THE INVENTION

Eukaryotic cells can shift from a proliferating state to a quiescent state only during a brief window of the cell cycle. Temin, *J. Cell. Phys.* 78:161 (1971). Thus, depending on their position in the cell cycle, cells deprived of mitogens such as those present in serum when mammalian cells are examined, will undergo immediate cell cycle arrest, or they will complete mitosis and arrest in the next cell cycle. The transition from mitogen-dependence to mitogen-independence occurs in the mid- to late-G1 phase of the cell cycle. Pardee, *Proc. Natl. Acad. Sci. USA* 71:1286 (1974), showed that many different anti-mitogenic signals cause the cell cycle to arrest at a kinetically common point, and further showed that the cell cycle becomes unresponsive to all of these signals at approximately the same time in mid- to late-G1. This point was named the restriction point, or R point.

Time-lapse cinematography of mitotically proliferating single cells has also been used to precisely map the timing of the cell cycle transition to mitogen-independence. This confirmed that mitogen depletion or other growth inhibitory signals cause post-mitotic, early-G1 cells to immediately exit the cell cycle, and that cell cycle commitment (autonomy from mitogenic signals), occurs in mid-G1 (Larsson et al., *J. Cell. Phys.* 139:477 (1989), and Zetterberg et al., *Proc. Natl. Acad. Sci. USA* 82:5365 (1985)). Together these observations (1985)). Together these observations show that the mitogen-dependent controls on cell proliferation are linked to cell cycle progression.

Transit through G1 and entry into S phase requires the action of cyclin-dependent kinases (Cdks) (Sherr, *Cell* 79:551 (1994)). Growth inhibitory signals have been shown to prevent activation of these Cdks during G1 (Serrano et al., *Nature* 366:704 (1993); Hannon and Beach, *Nature* 371:257 (1994); El-Deiry et al., *Cell* 75:89 (1993); Xiong et al., *Nature* 366:701 (1993); Polyak et al., *Cell* 78:59 (1994); Toyashima and Hunter, ibid., p. 67; Lee et al., *Genes & Dev.* 9:639 (1995); Matsuoka et al., ibid., p. 650; Koff et al., *Science* 260:536 (1993)). The catalytic activity of Cdks is known to be regulated by two general mechanisms, protein phosphorylation and association with regulatory subunits (Gould et al., *EMBO J.* 10:3297 (1991); Solomon et al., ibid., 12:3133 (1993); Solomon et al., *Mol. Biol. Cell* 3:13 (1992); Jeffrey et al., *Nature* 376:313 (1995); Morgan, *Nature* 374:131 (1995)). Among the regulatory subunits, the association of Cdks with inhibitory CKI subunits (Cyclin-dependent Kinase Inhibitors) has been most closely correlated with the effect of mitogen depletion on cell proliferation and Cdk activity.

Plant cells were used in early studies of cell growth and division to establish the phases of the eukaryotic cell cycle. (Howard et al., *Heredity* 6(suppl.):216–273 (1953)), but little is known about the molecular mechanisms of plant cell cycle regulation. Plant cells that cease dividing in vivo due to dormancy, or in vitro due to nutrient starvation, arrest at principal control points in G1 and G2. (van't Hof et al., in *The Dynamics of Meristem Cell Populations*, Miller et al. eds., Plenum, New York, pp 15–32 (1972), Gould et al., *Protoplasma* 106:1–13 (1981)). Generally, this pattern is in agreement with that seen in other eukaryotic systems. Homologues of cdc2 kinase have been isolated from a number of plant species, including pea (Feller et al., *Proc. Natl. Acad. ScL USA* 87:5397–5401 (1990)), alfalfa (Hirt et al., *Proc. Natl. Acad Sci USA* 88:1636–1640 (1991) and Hirt et al., *Plant J.* 4:61–69 (1993)), and from *A. thaliana*. (Ferreira et al., *Plant Cell* 3:531–540 (1991), Hirayama et al., *Gene* 105:159–165 (1991)), among others. Also, a number of cDNA sequences encoding plant cyclins with A-, B- or D-type characteristics or having mixed A- and B-type features have been isolated from various species, including carrot and soybean (Hata et al., *EMBO J.* 10:2681–2688 (1991)), and *Arabidopsis* (Hemerly et al., *Proc. Natl. Acad. Sci. USA* 89:3295–3299 (1992), and Soni et al., *Plant Cell* 7:85–103 (1995)), among others.

Recently DNA sequences encoding plant-cyclin dependent kinase inhibitors of *Arabidopsis* have been identified (WO 99/14331; Wang et al., *Plant J.* 15:501–510 (1998); each incorporated herein by reference). The proteins encoded by the DNA sequences have been suggested modulators of plant cell division because of their binding to cyclins and similar in vitro inhibitory effects on kinases. It has also been suggested that partial and/or total elimination of a gene or reducing the expression of a gene encoding a plant cyclin-dependent kinase inhibitor could influence and would likely inhibit cell division (WO 99/14331).

Genetic engineering of plants, which entails the isolation and manipulation of genetic material, and the subsequent introduction of that material into a plant, plant tissue, or plant cells, has changed plant breeding and agriculture considerably over recent years. Increased crop food values, higher yields, feed value, reduced production costs, pest resistance, stress tolerance, drought resistance, and the production of pharmaceuticals and biological molecules as well as other beneficial traits are all potentially achievable through genetic engineering techniques.

The ability to manipulate gene expression provides a means of producing new characteristics in transformed plants. For example, the ability to increase the size of a plant's root system would permit the increased nutrient assimilation from the soil. Moreover, the ability to increase leaf growth, i.e., an increase in leaf size and/or leaf number, would increase the capacity of a plant to assimilate solar energy. Obviously, the ability to control the growth of an entire plant, or specific target organs of a plant would be very desirable.

Cell cycle control genes can be employed to improve growth and development in the economically valuable portions of crop plants, including both dicotyledonous plants and monocotyledonous plants. In monocotyledons the additional use of cell cycle control genes or protein can be useful to improve their regenerability from callus.

Further, cell cycle control genes are potential sites to influence cell division and behavior at stages of plant development when cell number influences the final yield of economically valuable tissue. A specific example is the number of rounds of nuclear division at the multinucleate stage of endosperm development in cereal grains, or at the stage of fruit or flower development.

Based on the foregoing, it is clear that a need exists for methods for modulating the cell division of plant cells, plant tissues, and plants harboring one or more functionally inactivated endogenous cyclin inhibitor genes, and optionally also harboring a transgene encoding a heterologous cyclin inhibitor polypeptide or mutant variant cyclin inhibitor polypeptide which is expressed in at least a subset of host cells. Thus, it is an object of the invention herein to provide methods and compositions for increasing cell division by functionally inhibiting the expression or activity of plant cyclin inhibitors.

Further, the present invention provides for nucleic acid sequences encoding the plant D-like cyclin binding protein BRO4. Also, the present invention provides targeting transgenes to inactivate an endogenous cyclin inhibitor gene, particularly the genes which encode proteins having binding motifs for plant D-like cyclin and cyclin dependent kinases. It is also an object of the invention to provide methods to produce transgenic plant cells, plant tissues, and transgenic plants harboring a correctly targeted transgene of the invention. The methods may also be used to inactivate cyclin inhibitor genes in cells explanted from a plant (e.g., for ex vivo insertion), such as to impart to the resultant targeted cells a phenotype which results from an increased cell proliferation phenotype.

SUMMARY OF THE INVENTION

The present invention provides methods for modulating the cell cycle of plant cells such that growth and/or yield of a plant is increased as compared to a wild-type plant. The method comprises functionally inactivating a plant D-like cyclin inhibitor gene. Functional inactivation can be induced by genetic modification of the cyclin inhibitor gene, such as by, physical modification of the cyclin inhibitor gene, the insertion of a gene encoding an antisense molecule specific for a sequence encoding a cyclin inhibitor gene, or double stranded RNA induced silencing, i.e., (RNAi), and the like. The cell cycle can also be modulated by providing an inhibitor of the cyclin/cyclin dependent kinase complex formation, i.e., small molecules, antibodies, polyclonal and monoclonal, recombinant antigen binding proteins, and the like.

In yet another embodiment, the present invention provides a method for producing transgenic plants cells having an increased growth rate and/or yield as compared to a corresponding wild-type plant. The method comprises, contacting the plant cells with nucleic acid sequences which can functionally disrupt nucleic acid sequences encoding a cyclin inhibitor protein to obtain transformed plant cells; producing plants from the transformed plant cells, and selecting for plants which exhibit an increased growth rate or yield as compared to a wild-type plant. Within one specific embodiment, the cyclin inhibitor encoding gene is a BRO gene, i.e., the BRO4 gene or another plant cyclin inhibitor.

In still another embodiment, the present invention comprises a method for producing a plant characterized by having an increased growth rate and/or yield as compared to a wild-type plant, the method comprising contacting a plant with an agent which is an inhibitor of a cyclin inhibitor of the present invention. The agent prevents the cyclin inhibitor from interacting with a plant D-like cyclin/cyclin-dependent kinase complex and therefore allows the cell to continue to divide. Additional agents of the present invention can induce the expression of an inhibitor of the cyclin inhibitor protein.

The present invention also provides isolated plant cell populations and plants which have been treated with an inhibitor of a plant D-like cyclin inhibitor and, as such, have an increased proportion of dividing cells to non-dividing cells relative to the proportion in a population of untreated cells. The dividing cells, transgenic protoplasts, are particularly useful in generating transgenic whole plants.

Further, the present invention provides isolated polynucleotide sequences which encode a plant D-like cyclin binding protein designated BRO4. In one particular embodiment the protein also is capable of binding to and inactivating a plant cyclin/cyclin dependent kinase complex, i.e., a plant D-like cyclin inhibitor, and can be used to increase the proliferation of plant cells.

In another embodiment, the invention provides substantially purified plant D-like cyclin inhibitor protein encoded by polynucleotide sequence BRO4 of the present invention. The present invention further provides vectors which comprise the polynucleotide sequence which encode the amino acid sequence of the BRO4 cyclin inhibitor of the present invention, or the complement thereof. Host vector systems for the expression of a cyclin inhibitor of the present invention are also provided, wherein the inhibitor is capable of binding a plant D-like cyclin and plant D-like cyclin/cdk complex.

DESCRIPTION OF THE SPECIFIC EMBODIMENTS

Figure 1:
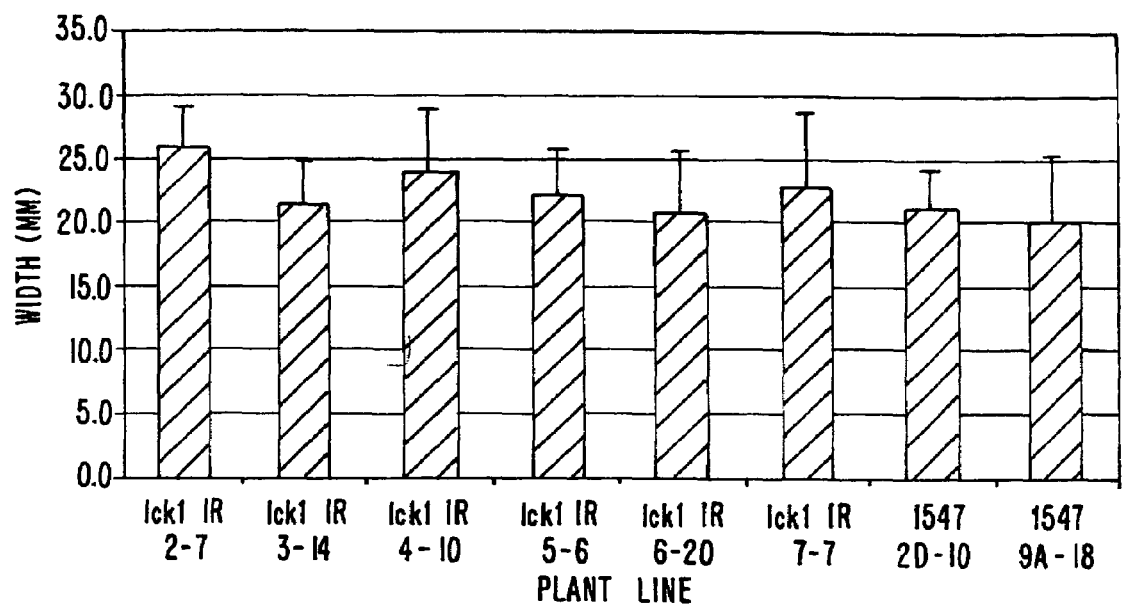
FIG. 1 depicts measurement of the width (mm) of the largest rosette leaf of various ICK-IR transgenic plant lines and control plants.

Prior to setting forth the invention, it may be helpful to an understanding thereof to set forth definitions of certain terms to be used hereinafter.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

"Cyclin inhibitor protein" or "cyclin inhibitor polypeptide" as used herein, refers to a protein or polypeptide which binds to and inactivates a cyclin-dependent kinase (CDK) or a related protein in the cyclin pathway in a cell. BRO3 and BRO4 proteins are examples of plant cyclin inhibitor proteins. A cyclin inhibitor gene as used herein is a polynucleotide sequence which encodes a plant cyclin inhibitor protein or polypeptide including all nucleotide sequences which comprise alternative nucleotides which encode the same amino acid sequence because of the degeneracy of the genetic code.

As used herein, the term "cyclin inhibitor gene" or "cyclin inhibitor gene locus" refers to a region of a chromosome spanning all of the exons which potentially encode a cyclin inhibitor polypeptide and extending through flanking sequences (e.g., including promoters, enhancers, and the like) that participate in cyclin inhibitor protein expression. Essentially any gene encoding a cyclin inhibitor protein may be disrupted including, but not limited to BRO3 (FL39), BRO4, ICK1, and the like. A particular embodiment of the present invention comprises the BRO4 gene, which can be disrupted, and, if desired, replaced with a cognate heterologous gene or minigene, i.e., by structural disruption or silencing.

The term "disrupted" as used herein means that a gene locus can be "structurally disrupted" so as to comprise at least one mutation or structural alteration such that the disrupted gene is incapable of directing the efficient expression of a functional gene product or the gene can be "functionally inactivated" such that a gene locus is either not expressed or is incapable of expressing a functional gene product. Functional inactivation can result from a structural disruption and/or interruption of expression at either the level of transcription or translation. Functional inactivation of an endogenous cyclin inhibitor gene, such as a Bro3 (FL39), BRO4, or ICK1 gene, can also be produced by other methods, e.g., antisense polynucleotide gene suppression, double stranded RNA induced gene silencing, and the like.

The term "corresponds to" is used herein to mean that a polynucleotide sequence that shares identity to all or a portion of a reference polynucleotide sequence. The term "complementary to" is used herein to mean that the sequence is complementary to all or a portion of a reference polynucleotide sequence.

The terms "substantially corresponds to", "substantially homologous", or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence.

Optimal alignment of sequences for comparison can be conducted, e.g., by the local homology algorithm of Smith et al., *Adv. Appl. Math.* 2:482 (1981), by the homology alignment algorithm of Needleman et al., *J. Mol. Biol.* 48:443 (1970), by the search for similarity method of Pearson et al., *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), or by visual inspection.

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng et al. *J. Mol. Evol.* 35:351–360 (1987). The method used is similar to the method described by Higgins et al., *CABIOS* 5:151–153 (1989). The program can align up to 300 sequences, each of a maximum length of 5,000 nucleotides or amino acids. The multiple alignment procedure begins with the pairwise alignment of the two most related sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their nucleotide or amino acid coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identic and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as for as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and the speed of the alignment. The BLAST program uses as defaults a wordlength (W) of 11, the BLOSUM62 scoring matrix (see, Henikoff et al., *Proc. Natl. Acad. Sci. USA* 89:10915 (1989)) alignments (B) of 50, expectation (E) of 10, M=5, N=−4, and a comparison of both strands.

In addition to calculating percent sequence identity, the BLAST algorithm also performs statistical analysis of the similarity between two sequences (see e.g., Karlin et al., *Proc. Natl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison test is less than about 0.1, more preferably less than about 0.01, and most preferably less than about 0.001.

In general, targeting efficiency increases with the length of the targeting transgene portion (i.e., homology region) that is substantially complementary to a reference sequence present in the target DNA (i.e., crossover target sequence). In general, targeting efficiency is optimized with the use of isogenic DNA homology clamps, although it is recognized that the presence of various recombinases may reduce the degree of sequence identity required for efficient recombination.

The term "nonhomologous sequence", as used herein, has both a general and a specific meaning; it refers generally to a sequence that is not substantially identical to a specified reference sequence, and, where no particular reference sequence is explicitly identified, it refers specifically to a sequence that is not substantially identical to a sequence of at least about 50 contiguous bases at a targeted endogenous cyclin inhibitor gene, such as a BRO4 gene.

Specific hybridization is defined herein as the formation of hybrids between a targeting transgene sequence (e.g., a polynucleotide encoding a plant D-like cyclin inhibiting protein which may include substitutions, deletion, and/or additions) and a specific target DNA sequence (e.g., a BRO3 (FL39), ICK1, or BRO4 gene sequence), wherein a labeled targeting transgene sequence preferentially hybridizes to the target such that, for example, a single band corresponding to a restriction fragment of a genomic cyclin inhibitor gene can be identified on a Southern blot of DNA prepared from cells using said labeled targeting transgene sequence as a probe. It is evident that optimal hybridization conditions will vary depending upon the sequence composition and length(s) of the targeting transgene(s) and endogenous target(s), and the experimental method selected by the practitioner. Various guidelines can be used to select appropriate hybridization conditions (see, Sambrook et al., *Molecular Cloning: A Laboratory Manual* (1989), 2nd Ed., Cold Spring Harbor, N.Y. and Berger and Kimmel, *Methods in Enzymology Volume 152, Guide to Molecular Cloning Techniques* (1987), Academic Press, Inc., San Diego, Calif., which are incorporated herein by reference).

The term "naturally-occurring" as used herein as applied to an object refers to an object that can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of plants which may have been selectively bred according to classical genetics are considered naturally-occurring plants.

The term "homologue" as used herein refers to a gene sequence that is evolutionarily and functionally related between species.

As used herein, the term "targeting construct" refers to a polynucleotide which comprises: (1) at least one homology region having a sequence that is substantially identical to or substantially complementary to a sequence present in a host cell endogenous plant D-like cyclin inhibitor gene locus, and (2) a targeting region which becomes integrated into an host cell endogenous plant D-like cyclin inhibitor gene locus by homologous recombination between a targeting construct homology region and said endogenous cyclin inhibitor gene locus sequence. If the targeting construct is a "hit-and-run" or "in-and-out" type construct (Valancius and Smithies, *Mol. Cell. Biol.* 11: 1402 (1991); Donehower et al., *Nature* 356:215 (1992); which are incorporated herein by reference), the targeting region is only transiently incorporated into the endogenous cyclin inhibitor gene locus and is eliminated from the host genome by selection. A targeting region can comprise a sequence that is substantially homologous to an endogenous cyclin inhibitor gene sequence and/or can comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein refer to a segment (i.e., a portion) of a targeting construct having a sequence that substantially corresponds to, or is substantially complementary to, a predetermined endogenous plant D-like cyclin inhibitor gene sequence, which can include sequences flanking said cyclin inhibitor gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence.

The terms "homology clamp" and "homology region" are interchangeable as used herein, and the alternative terminology is offered for clarity, in view of the inconsistent usage of similar terms in the art. A homology clamp does not necessarily connote formation of a base-paired hybrid structure with an endogenous sequence. Endogenous plant D-like cyclin inhibitor gene sequences that substantially correspond to, or are substantially complementary to, a transgene homology region are referred to herein as "crossover target sequences" or "endogenous target sequences."

As used herein, the term "correctly targeted construct" refers to a portion of the targeting construct which is integrated within or adjacent to an endogenous crossover target sequence, such as a portion of an endogenous BRO4 gene locus. It is possible to generate cells having both a correctly targeted transgene(s) and an incorrectly targeted transgene(s). Cells and plants having a correctly targeted transgene(s) and/or an incorrectly targeted transgene(s) may be identified and resolved by PCR and/or Southern blot analysis of genomic DNA.

As used herein, the term "targeting region" refers to a portion of a targeting construct which becomes integrated into an endogenous chromosomal location following homologous recombination between a homology clamp and an endogenous plant D-like cyclin inhibitor gene, such as a BRO4 gene sequence. Typically, a targeting region is flanked on each side by a homology clamp, such that a double-crossover recombination between each of the homology clamps and their corresponding endogenous plant D-like cyclin inhibitor gene sequences results in replacement of the portion of the endogenous plant D-like cyclin inhibitor gene locus by the targeting region; in such double-crossover gene replacement targeting constructs the targeting region can be referred to as a "replacement region". However, some targeting constructs may employ only a single homology clamp (e.g., some "hit-and-run"-type vectors, see, Bradley et al. *Bio/Technology* 10:534 (1992), incorporated herein by reference).

The term "agent" is used herein to denote a chemical compound, a mixture of chemical compounds, a biological macromolecule, i.e., an antibody, polyclonal or monoclonal specific for a plant D-like cyclin inhibitor, or an extract made from biological materials such as bacteria, plants, fungi, or animal (particularly plant) cells or tissues.

The term "cyclin inhibitor knockout phenotype" refers to a phenotypic characteristic present in cyclin inhibitor gene +/− and −/− plants (e.g., *Arabidopsis* hemizygous or homozygous for functionally inactivated cyclin inhibitor alleles, i.e., a BRO family gene, for example, BRO4.) and absent in wild-type plants of the same species, strain, and age when raised under the same conditions. Examples include those described herein, e.g., hyperplasia, overall hypertrophy, hyperplastic, hypercellular and other phenotypic characteristics noted herein when compared to the wild-type phenotype.

The term "plant cell" as used herein refers to protoplasts, gamete producing cells, and cells which can regenerate whole plants. As used herein, the term "plant" refers to either a whole plant, a plant cell or a group of plant cells, such as plant tissue or plant seed. Platelets are also included within the meaning of "plant". Plants included in the invention are any plants, particularly economically important plants, amenable to gene transfer techniques, including gymnosperms and angiosperms, both monocotyledons and dicotyledons.

Examples of monocotyledonous angiosperms include, but are not limited to, asparagus, field and sweet corn, barley, wheat, rice, sorghum, onion, millet, rye and oats and other cereal grains. Examples of dicotyledonous angiosperms include, but are not limited to, tomato, tobacco, cotton, rapeseed, field beans, soybeans, peppers, lettuce, and the like. Examples of woody species include poplar, pine, cedar, oak, and the like.

The term "genetic modification" as used herein refers to the introduction of one or more exogenous nucleic acid sequences (i.e., a heterologous gene), e.g., a plant D-like cyclin inhibitor encoding sequence, as well as regulatory sequences into one or more plant cells, which can generate whole, sexually competent, viable plants. The term "genetically modified" as used herein refers to a plant which has been generated through the aforementioned process.

A preferred method of introducing the nucleic acid sequences, for example a desired heterologous gene, into plant cells is to infect a plant cell, an explant, a meristem or a seed with *Agrobacterium tumefaciens* previously transformed with the nucleic acid sequence. Under appropriate conditions known in the art, the transformed plant cells are grown to from shoots, roots, and develop further into plants. The nucleic acid sequence can be introduced into appropriate plant cells, for example, by means of the Ti or Ri plasmid of *Agrobacterium tumefaciens*. The Ti or Ri plasmid is transmitted to plant cells upon infection by *Agrobacterium tumefaciens*, and is stably integrated into the plant genome (Horsch et al., *Science* 233:496–498 (1984); Fraley et al., *Proc. Natl. Acad. Sci. USA* 80:4803(1983), incorporated herein by reference). One *Agrobacterium* method is in planta *Agrobacterium*-mediated gene transfer by infiltration, e.g., of adult *Arabidopsis thaliana* plants; Bechtold et al., *C. R. Acad. Sci. Life Sciences* 316:1194–1199 (1993), incorporated herein by reference).

All plant cells which can be infected and subsequently transformed by *Agrobacterium* and whole plants regenerated from the transformed cells can also be transformed according to the invention so as to produce transformed whole plants which contain the transferred nucleic acid sequence. Plant cells can be transformed with *Agrobacterium* in various ways, including: co-cultivation of *Agrobacterium* with cultured isolated protoplasts, transformation of cells or tissues with *Agrobacterium*, or transformation of seeds, apices or meristems with *Agrobacterium*.

In transformation of plants with *A. tumifaciens* a transforming DNA (T-DNA) is typically modified to incorporate a nucleic acid sequence encoding a desired heterologous gene. The recombinant T-DNA contains the desired heterologous gene between flanking non-coding regulatory sequences and the left and right border regions of the wild-type tumor-inducing (Ti) plasmid. The recombinant T-DNA can be provided as part of an integrative plasmid, which integrates into a wild-type Ti plasmid by homologous recombination. Typically, however, the recombinant T-DNA is provided in a binary vector and transferred into a plant cell through the action of trans-acting vir genes on a helper Ti plasmid. The T-DNA integrates randomly into the nuclear genome with some of the transformants permitting expression of the desired protein. Selection of transformants can also be made by selection of a phenotypic marker. These phenotypic markers include, but are not limited to, antibiotic resistance, herbicide resistance or visual observation. Other phenotypic markers are known in the art and may be used in this invention.

If naked nucleic acid introduction methods are chosen, then the vector need be no more than the minimal nucleic acid sequence necessary to confer the desired traits, without the need for additional other sequences. Thus, the possible vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, mini-chromosome vectors, and viral vectors, including the possibility of RNA forms of the gene sequences. The selection of vectors and methods to construct them are commonly known to persons of ordinary skill in the art and are described in general technical references (Bai et al., *Methods in Enzymology*, supra).

However, any additional vector sequences that confer resistance to degradation of the nucleic acid sequence to be introduced and that assist in the process of genomic integration or provide a means to easily select for those cells or plants which are actually, in fact, transformed are advantageous and greatly decrease the difficulty of selecting useable transgenotes.

All transformable plants from which whole regenerated plants can be generated are useful in the present invention. Monocots may be transformed with *Agrobacterium* by electroporation (Fromm et al., *Nature* 319:791–793 (1986); Rhodes et al. *Science* 240:204–207 (1988)); by direct gene transfer (Baker et al., *Plant Genetics* 201–211 (1985)); by using pollen-mediated vectors (EP 0 270 356); and by injection of DNA into floral tillers (de la Pena et al., *Nature* 325:274–276 (1987), all incorporated herein by reference).

Another method for introducing a nucleic acid fragment encoding a cyclin inhibitor gene into a plant cell is high velocity ballistic penetration by small particles with the nucleic acid sequence to be introduced contained either within the matrix of such particles, or on the surface thereof. (Klein et al., *Nature* 327:70 (1970). Bombardment transformation methods are also described in Sanford et al. (*Techniques* 3:3–16 (1991) and Klein et al., *Bio/Techniques* 10:286 (1992)). Although typically only a single introduction of a new nucleic acid sequence is required this method particularly provides for multiple introductions.

Other viruses which infect certain types of plants can also be used to insert nucleic acid fragments. For example, Cauliflower mosaic virus (CaMV) can also be used. (U.S. Pat. No. 4,407,956, incorporated herein by reference). CaMV viral DNA genome is inserted into a parent bacterial plasmid creating a recombinant DNA molecule which can be propagated in bacteria. After cloning, the recombinant plasmid again can be cloned and further modified by introduction of the desired nucleic acid sequence. The modified viral portion of the recombinant plasmid is then excised from the parent bacterial plasmid, and used to transform or transfect the plant cells or plants.

Normally, a plant cell is regenerated to obtain a whole plant from the transformation process. The immediate product of the transformation is referred to as a "transgenote". Regeneration from protoplasts varies from species to species of plants, but generally, a suspension of protoplasts is first made. In certain species, embryo formation can then be induced from the protoplast suspension. The culture media will generally contain various amino acids and hormones, necessary for growth and regeneration. Examples of hormones utilized include auxins and cytokinins. Efficient regeneration will depend on the medium, on the genotype, and on the history of the culture. If these variables are controlled, regeneration is reproducible.

Regeneration also occurs from plant callus, organs and parts. Transformation can be performed in the context of plant part regeneration. (see, Methods in Enzymology 118, and Klee et al., Ann. Rev. Plant Physiol. 38:467 (1987)). Utilizing the leaf disk-transformation-regeneration method of Horsch et al., Science 227:1229 (1985), disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants can be propagated by utilizing cuttings or tissue culture techniques to produce multiple identical plants. Selection of desirable transgenotes is made and new varieties are obtained and propagated vegetatively for commercial use.

In seed propagated crops, mature transgenic plants can be self crossed to produce a homozygous inbred plant. The resulting inbred plant produces seed containing the newly introduced foreign gene(s). These seeds can be grown to produce plants that would produce the selected phenotype, e.g., increased size and/or yield.

Parts obtained from regenerated plants, such as flowers, seeds, leaves, branches, roots, fruit, and the like are encompassed as part of the present invention, provided that these parts comprise plant cells that have been transformed as described. Progeny and variants and mutants of the regenerated plants are also included within the scope of the invention, provided that these parts comprise the introduced nucleic acid sequences.

An "isolated" nucleic acid, polynucleotide or polypeptide is a nucleic acid, polynucleotide or polypeptide which is substantially separated from other contaminants that naturally accompany it, e.g., protein, lipids, and other nucleic acid and/or polynucleotide sequences. The term embraces nucleic acid or polynucleotide sequences which have been removed or purified from their naturally-occurring environment or clone library, and include recombinant or cloned DNA isolates and chemically synthesized analogues or analogues biologically synthesized by heterologous systems.

The subject invention provides a family of genes, designated herein as BRO, which encode protein products capable of binding a plant cyclin. In a specific embodiment the protein gene product is capable of binding to a plant cyclin and of inhibiting the activity of a plant cyclin/cyclin-dependent kinase complex.

In one embodiment, the members of the BRO gene family encode an amino acid sequence domain comprising about 5 to about 10 amino acid residues, which domain is the plant cyclin binding domain. The consensus binding domain for a plant D-like cyclin comprises the sequence Glu $Xaa_1$ $Xaa_2$ $Xaa_3$ $Xaa_4$ Phe, wherein $Xaa_1$ can be Leu, Ile or another hydrophobic amino acid residue, $Xaa_2$ can be Glu or Asp, $Xaa_3$ can be Leu, Arg, Asp or any other amino acid residue, and $Xaa_4$ can be Phe, Leu, or another hydrophobic amino acid residue (SEQ ID NO: 9). This domain is located from about 15 to about 30 amino acid residues from the cyclin-dependent kinase binding domain described herein below, when the cyclin-dependent kinase binding domain is present.

Members of the BRO gene family further encode a protein comprising an amino acid sequence which binds specifically to a cyclin dependent kinase and which is capable of inhibiting the activity of the cyclin/cdk complex in cell cycle regulation. The amino acid sequence encoding the cyclin dependent kinase motif is homologous to that of a cyclin-dependent kinase of mammalian cells and generally comprises the amino acid residue sequence:

Lys Tyr Asn Phe Asp $Xaa_1$ $Xaa_2$ $Xaa_3$ $Xaa_4$ $Xaa_5$ Pro Leu $Xaa_6$ $Xaa_7$ Gly Arg Tyr $Xaa_8$ Trp $Xaa_9$ $Xaa_{10}$ Leu $Xaa_{11}$;

wherein $Xaa_1$ can comprise Phe or Ile, $Xaa_2$ can comprise Glu or Val, $Xaa_3$ can comprise Lys or Asn, $Xaa_4$ can comprise Asp or Glu, $Xaa_5$ can comprise Glu or Lys, $Xaa_6$ can comprise Gly or Glu, $Xaa_7$ may be absent or can comprise Gly, $Xaa_8$ can comprise Glu or Lys, $Xaa_9$ can comprise Val or Asp, $Xaa_{10}$ can comprise Lys or Arg, $Xaa_{11}$ can comprise Asn or Glu (SEQ ID NO: 10). Certain other substitutions within the sequence are acceptable as long as the protein is capable of binding a plant cyclin and is capable of inhibiting the activity of the cyclin cdk complex.

Inhibition of the activation of a plant cyclin/cdk complex can be measured, for example, using assays for (a) the site specific phosphorylation of the cdk moiety or the plant cyclin/cdk complex, and (b) protein kinase activity. Such assays are described more fully herein. These assays can be conducted in a kinetic mode, i.e., measuring the rate of phosphorylation, or as qualitative or quantitative static assays, i.e., measurements made at selected points in time. Those skilled in the art will recognize that a variety of enzymes and conditions can be used in such assays.

Plant D-like cyclin inhibitor genes of the present invention can be obtained, by way of example, by use of a yeast two hybrid screen. Methods for practicing a yeast two hybrid screen are described in, for example, Fields and Stemglanz Trends in Genetics 10:286–292 (1994); and Bai et al., Methods in Enzymology 273:331–347 (1996). Generally, the yeast two hybrid system was devised to identify genes encoding proteins that physically associate with a target protein in vivo. In a preferred embodiment, the "bait" construct comprises an expression vector encoding a DNA-binding domain, i.e., the GAL4 DNA-binding domain vector pAS1, pAS2, pGBT9, or the like, fused to the nucleotide sequence encoding a plant cyclin. In a particularly preferred embodiment, the "bait" construct encodes a plant D-like cyclin. A cDNA fusion library can then be made from the plant of interest, i.e., from *Arabidopsis thaliana* with the GAL4 activation domain, i.e., the GAL4 activation domain vector pACT1, pACT2, or the like. The two fusion plasmids can then be transformed into a yeast reporter strain. Identification is made of those yeast cells which contain nucleotide sequences from the *Arabidopsis* library which interacts with a plant D-like cyclin, and the like. The cDNA fragments encoding members of the BRO cyclin inhibitor family of genes can then be isolated and identified.

Alternatively, a genomic library from a whole plant, a plant tissue or plant cells can be probed with, for example, a consensus-degenerate hybrid oligonucleotide primer (CODEHOP) for amplification of distantly-related sequences as described by Rose et al. (*Nuc. Acids Res.* 26:1628–1635 (1998); incorporated herein by reference). Briefly, a primer comprising a short 3' degenerate core region and a longer 5' consensus clamp region is used for PCR amplification. With this method only 3–4 highly conserved amino acid residues are necessary for design of the core sequence, which is stabilized by the clamp during annealing to template molecules. In a specific embodiment, a nucleotide sequence from the cyclin binding domain of a BRO family gene is used to generate a 5' consensus clamp region of from about 18 to about 25 base pairs. An approximately 11 to 12 base pair degenerate 3' core region can be designed based on one of the BRO gene sequences provided as SEQ ID NO: 1, SEQ ID NO:3, SEQ ID NO: 5, and SEQ ID NO: 7. The CODEHOP program is available at http://blocks.fhcrc.org/codehop.html, and is directly linked from the BlockMaker multiple sequence alignment site for hybrid primer prediction beginning with a set of related protein sequences.

Primers can be synthesized by any method known to the skilled artisan. Genomic DNA can be extracted from a plant source, for example, using commercially available kits designed for plant DNA. Whole PCR products can be cloned using any of a number of cloning plasmid vehicles and analyzed by, for example, agarose gel electrophoresis and DNA sequencing using standard methods (Sambrook et al., *Molecular Cloning, A Laboratory Manual*, 2nd ed., Cold Spring Harbor Laboratory Press, Cold Spring Harbor, N.Y. (1989); Ausubel et al., *Current Protocols in Molecular Biology*, Wiley, New York (1994)). Dendrograms can be produced using the neighbor-joining and bootstrapping procedures in ClustralW (Thompson et al., *Nuc. Acids Res.* 22:4673–4680 (1994)) as implemented on the BLOCKS world wide web site (Lisitsyn et al., *Science* 259:946–951 (1993); http://blocks.fhcrc.org).

In general, a transcribable plant D-like cyclin inhibitor polynucleotide sequence or its reverse complement contain an operably linked promoter capable of functioning in the plant cell into which the polynucleotide is to be transferred. Examples of plant-functional promoters include, but are not limited to, CaMV 35S, tomato E8, patatin, ubiquitin, mannopine synthase (mas), rice actin 1, soybean seed protein glycinin (Gyl), and soybean vegetative storage protein (vsp). Many hybrid promoters such as Mac comprising elements of the CAMV 35S combined with the 3' region of mannopine synthase promoter (Comai et al., *Plant Mol. Biol.* 15:373–381 (1990); incorporated herein by reference) are also useful in the present invention.

The transcribable plant D-like cyclin inhibitor polynucleotide sequence is typically at least 25 nucleotides long, more usually at least 50–100 nucleotides long, frequently at least 100–250 nucleotides long, often at least 500 nucleotides long or longer, up to the length of the complete endogenous gene (spanning promoter through transcription termination sequence/polyadenylation site). The transcribable cyclin inhibitor sequence is positioned relative to the promoter such that a RNA transcript of the transcribable sequence is the same or the reverse complement polarity as the mRNA transcript of the endogenous gene (i.e., sense or antisense orientation).

The polynucleotide encoding the plant D-like cyclin inhibitor can be part of a larger polynucleotide, such as a transgene having a selectable marker to identify cells having integrated the transgene, or a homologous recombination construct having selectable marker(s) and homology regions for targeting the inhibitor polynucleotide to a predetermined location in the genome of cells. Polynucleotides encoding the inhibitor can be in the form of a heterologous expression cassette in a transfectant cell or transgenic cell. Often, the polynucleotide encoding the inhibitor is obtained as a vector produced with DNA isolated from a cloned copy (or portion thereof) of the target endogenous gene. The inhibitor polynucleotide sequence is usually isolated as part of a genomic gene clone, although in some embodiments a cDNA clone (or portion thereof) of the target protein to be inhibited can be employed (for general cDNA methods see, Goodspeed et al., *Gene* 76:1 (1989); Dunn et al., *J. Biol. Chem.* 264:13057 (1989), both incorporated herein by reference).

Vectors containing an inhibitor polynucleotide sequence are typically grown in bacteria, such as *E. coli*, and then isolated using standard molecular biology methods, or may be synthesized as oligonucleotides. Direct polynucleotide synthesis and ligation can be carried out (if necessary) which does not require prokaryotic or eukaryotic vectors. Polynucleotides (and transgenes comprising such) can be transferred to host cells by any suitable technique, including vacuum infiltration of transformed cells into an intact plant (Bechtold et al. *C. R. Acad. Sci. la Vie/Life Sci.* 316: 1194–1199 (1993), incorporated herein by reference), microinjection, electroporation, lipofection, biolistics, calcium phosphate precipitation, and viral-based vectors, among others (e.g., U.S. Pat. Nos. 5,442,052, 5,354,854, 5,278,057, 5,262,316, 5,137,817, and 4,962,028, all incorporated herein by reference).

Cyclin Inhibitors

Cyclin inhibitors of the present invention that prevent the activation of a plant cyclin/cdk complex can be identified in a variety of screening assay formats. Inhibitors of cyclin mediated activation of a plant cyclin/cdk complex can be screened, for example, using an assay in which test substances are exposed to a suitable amount of plant cyclin, i.e., a plant D-like cyclin, and a plant cyclin-dependent kinase under conditions that permit the formation of active plant cyclin/cdk complexes. The active plant cyclin/cdk complex formed are then quantitated and compared to the inactive complexes formed in the absence of the test substance. Test substances that result in decreased active complexes compared to active complexes in the absence of the test substance are cyclin inhibitors.

Within a further embodiment, inhibitors of cyclin inhibitors can also be detected. Screening for said substances comprises, for example, using an assay in which test substances are exposed to suitable amounts of cyclin inhibitor, plant cyclin, i.e., a plant D-like cyclin, and a cyclin-dependent kinase under conditions that permit the formation of active plant cyclin/cdk complexes in the absence of cyclin inhibitor. The active plant cyclin/cdk complexes formed are then quantitated and compared to the quantity of active complexes formed in the absence of the test substance. Test substances that result in increased active complexes compared to active complexes in the absence of the test substance are inhibitors of the cyclin inhibitor.

Substances which can serve as inhibitors of the activity of a BRO family cyclin inhibitor include, but are not limited to, a) compounds capable of inhibiting the BRO-mediated inhibition of plant D-like cyclin/cdk complex activation, which can be identified as described above, b) compounds that specifically inhibit the interaction between a BRO family protein and plant cyclin/cdk complex, but not the site-specific phosphorylation of the cdk moiety of the cyclin/cdk complex in the absence of a BRO cyclin inhibitor, c) compounds that degrade or inactivate the BRO cyclin inhibitor protein, and d) compounds that interfere with the expression of BRO cyclin inhibitor protein, and the like. Such agents may include chemical compound inhibitors of a BRO cyclin inhibitor protein, including for example, small molecules, peptides, peptide memetics and the like, cyclin inhibitor antagonists, and molecules that inhibit the expression of a BRO family cyclin inhibitor, such as triplex forming oligonucleotides, antisense oligonucleotides, e.g., genomic and synthetic antisense molecules, ribozymes, RNAi, and the like.

For use as a BRO gene family inhibitor in the present invention to mediate cell cycle progression, the triplex forming oligonucleotides are BRO sequence-specific DNA binding agents that interfere with the transcription of a BRO family gene. Triplex-forming oligonucleotides are generally described in Maher, *Bioassays* 14:807–815 (1992); Gee et al., *Gene* 149:109–114 (1994); Noonberg et al., *Gene* 149: 123–126 (1994); Song et al., *Ann. NY Acad. Sci.* 761:97–108 (1995); Westin et al., *Nuc. Acids. Res.* 23:2184–2191 (1995); and Wand and Glazer, *J. Biol. Chem.* 207:22595–22901 (1995) each incorporated herein by reference. These oligonucleotides form triple helical complexes, under physiological conditions, on double-stranded DNA selectively inhibiting transcription of a cyclin inhibitor gene by physically blocking RNA polymerase or transcription factor access to the cyclin inhibitor gene DNA template. See also, e.g., WO 95/25818; WO 95/20404; WO 94/15616; WO 94/04550; and WO 93/09788, each of which is incorporated herein by reference. The triplex forming oligonucleotides targeted to the BRO4 gene or ICK1 gene may contain either a nucleotide or non-nucleotide tail to enhance the inhibition of transcription factor binding.

Antisense oligonucleotides that interfere with the expression of a cyclin inhibitor gene of the present invention and permit progression through the cell cycle, as exemplified in the Examples described below, are particularly useful in the present invention. Cyclin inhibitor gene antisense oligonucleotides, specifically for BRO4 or ICK1, are identified using methods, e.g., as described in detail in the Examples. The use of antisense oligonucleotides and their applications are described generally in, for example, Mol and Van der Krul, eds., *Antisense Nucleic Acids and Proteins Fundamentals and Applications*, New York, N.Y., 1992, which is incorporated by reference herein in its entirety.

Antisense as used herein includes both genetic and synthetic antisense molecules as provided herein below. Suitable antisense oligonucleotides are at least 11 nucleotides in length and up to and including the upstream untranslated and associated coding sequences of a cyclin inhibitor gene. As will be evident to one skilled in the art, the optimal length of antisense oligonucleotides is dependent on the strength of the interaction between the antisense oligonucleotides and their complementary sequence on the mRNA, the temperature and ionic environment translation takes place, the base sequence of the antisense oligonucleotide, and the presence of secondary and tertiary structure in the mRNA and/or in the antisense oligonucleotide.

Suitable target sequences for antisense oligonucleotides include intron-exon junctions (to prevent proper splicing), regions in which DNA/RNA hybrids will prevent transport of mRNA from the nucleus to the cytoplasm, initiation factor binding sites, ribosome binding sites, and sites that interfere with ribosome progression. A particularly preferred target region for antisense oligonucleotide is the 5' untranslated region of a cyclin inhibitor gene.

Further, double stranded RNA gene silencing (RNAi) can be used to functionally inhibit or silence expression of a plant D-like cyclin inhibitor. Genes can be engineered which contain an inverted repeat of a plant D-like cyclin inhibitor, i.e., BRO4 or ICK1, containing a stem structure of 100 to 300 base pairs, a loop structure comprising 200 to 500 base pairs encoding a segment of the cyclin inhibitor, and the inverted repeat region of the stem structure complementary to the stem structure which will form the double stranded stem. The construct can be spliced into a plasmid comprising a plant-functional promoter, i.e., CaMV 35S, tomato E8, patatin, ubiquitin, mannopine synthase, rice actin 1, soybean seed protein glycinin (Gy1) and soybean vegetative storage protein. Further, hybrid promoters, such as Mac comprising elements of the CaMV 35 and the mannopine synthase 3' region, or a tissue specific promoter. After amplification the construct can introduced into a transfer vector, such as an *Agrobacterium* vector, which is used to transform plants or plant cells.

Methods for controlling the expression of certain plant genes can be used to modify a plant's phenotype as desired, such as controlling the rate or time at which fruit ripening occurs or even the growth rate of a plant, plant tissue, or cells. One way to control expression of endogenous plant genes is the inhibition of specific gene expression by antisense suppression (U.S. Pat. Nos. 5,457,281, 5,453,566, 5,365,015, 5,254,800, 5,107,065, and 5,073,676), and an alternative method to inhibit expression of specific genes is sense suppression (U.S. Pat. Nos. 5,283,184, 5,231,020, and 5,034,323), each of said patents being incorporated herein by reference.

Antisense polynucleotides targeted to a plant cyclin inhibitor gene are prepared by inserting a DNA molecule containing the target DNA sequence into a suitable expression vector such that the DNA molecule is inserted downstream of a promoter in a reverse orientation as compared to the gene itself. The expression vector may then be transduced, transformed or transfected into a suitable cell resulting in the expression of antisense polynucleotides.

Alternatively, antisense oligonucleotides can be synthesized using standard manual or automated synthesis techniques. Synthesized oligonucleotides may be introduced into suitable cells by a variety of means including electroporation (e.g., as described in Yang et al., *Nucl. Acids. Res.* 23:2803–2810 (1995)), calcium phosphate precipitation, microinjection, poly-L-ornithine/DMSO (Dong et al., *Nucl. Acids. Res.* 21:771–772 (1993)). The selection of a suitable antisense oligonucleotide administration method will be evident to one skilled in the art. With respect to in vitro synthesized oligonucleotides, the stability of antisense oligonucleotides-mRNA hybrids may be increased by the addition of stabilizing agents to the oligonucleotide. Stabilizing agents include intercalating agents that are covalently attached to either, or both ends, of the oligonucleotide. Oligonucleotides may be made resistant to nucleases by, for example, modifications to the phosphodiester backbone by the introduction of phosphotriesters, phosphonates, phosphorothioates, phosphoroselenoates, phosphoramidates or phosphorodithioates. Oligonucleotides may also be made nuclease resistant by the synthesis of the oligonucleotides with alpha-anomers of the deoxyribonucleotides, as generally described in Mol and Van der Krul, supra.

For oligonucleotide-based inhibitors, the choice of a suitable sequence will be guided by, for example, the type of inhibitor (i.e., triplex forming oligonucleotide or antisense oligonucleotide) and the species to be treated. It may be preferable to choose sequences that are conserved between species to permit use in readily available models. Antisense oligonucleotides to sequences within BRO gene that are conserved can be chosen for use in the models.

The present invention also provides compositions and methods for inhibiting the expression of a member of the BRO gene family and thereby permitting cell cycle progression using ribozymes. The ribozymes can be administered in a variety of ways, including by genes targeted to a desired cell. A ribozyme of the invention targets the RNA transcripts of a BRO family gene. Each ribozyme molecule contains a catalytically active segment capable of cleaving a cyclin inhibitor RNA, and further comprises flanking sequences having a nucleotide sequence complementary to portions of the targeted RNA. The flanking sequences serve to anneal the ribozyme to the RNA in a site-specific manner. Absolute complementarity of the flanking sequences to the target cyclin inhibitor sequence is not necessary, however, as only an amount of complementarity sufficient to form a duplex with the target RNA and to allow the catalytically active segment of the ribozyme to cleave at the target sites is necessary. Thus, only sufficient complementarity to permit the ribozyme to be hybridizable with the target RNA is required.

As used herein, the term "ribozyme" means an RNA molecule having an enzymatic activity that is able to cleave or splice other separate RNA molecules in a nucleotide base sequence specific manner. By reference to catalytic or enzymatic RNA molecule is meant an RNA molecule which has complementarity in a substrate binding region to a specific BRO4 RNA target, and also has enzymatic activity that is active to cleave and/or splice RNA in that target, thereby altering the target molecule.

In certain embodiment of the present invention the enzymatic RNA molecule is formed in a hammerhead motif, but the ribozyme may also be formed in the motif of a hairpin, hepatitis delta virus, group I intron or RNAse P RNA (in association with an RNA guide sequence). Examples of hammerhead motifs are described by Rossi et al., *AIDS Res. Hum. Retrovir.* 8:183 (1992), hairpin motifs are described by Hampel et al., *Biochem.* 28:4929 (1989) and Hampel et al., *Nucl. Acids Res.* 18:299 (1990), the hepatitis delta virus motif is exemplified in Perrotta and Been, *Biochem.* 31:16 (1992), an RNAse P motif is described in Guerrier-Takada et al., *Cell* 35:849 (1983), and examples of the group I intron motif are described in Cech et al., U.S. Pat. No. 4,987,071, each of the foregoing disclosures being incorporated herein by reference. These specific motifs are not limiting in the present invention and those of skill in the art will recognize that an enzymatic RNA molecule of the invention has a specific substrate binding site which is complementary to one or more of the target cyclin inhibitor RNA regions and that it has nucleotide sequences within or surrounding that substrate binding site which impart an RNA cleaving activity to the molecule.

The flanking sequences upstream and downstream of the ribozyme catalytic site may comprise segments of any length that effectively imparts the desired degree of targeting specificity for the ribozyme. Preferably a flanking sequence comprises from about 4 to about 24 nucleotides, more preferably from about 6 to about 15 nucleotides, and typically about 9 to 12, and results in base pairing to the substrate sequence immediately upstream and downstream of the cyclin inhibitor RNA sequences, i.e., BRO3 or BRO4, which comprise the cleavage site.

Mutations which provide reduced function plant D-like cyclin inhibitor proteins can also be identified by methods such as TILLING (Targeting Induced Local Lesions In Genomes; *Nat. Biotechnol.* 18:455–457 (2000); incorporated herein by reference), wherein plants can be mutagenized with, for example ethyl methanesulfonate (EMS), and the plants exhibiting a hyperplastic phenotype, i.e., more and/or larger leaves, flowers, seed containing structures, fruit, and the like, can be screened for mutations in plant D-like cyclin inhibitor genes of known sequence, by for example heteroduplex formation.

The following examples are offered by way of illustration, not by way of limitation.

EXAMPLE 1

In this example a yeast two hybrid screen is used to isolate cDNA which encode proteins that interact with *Arabidopsis thaliana* D-type cyclins, D1 and D2. Yeast two-hybrid screens are reviewed as disclosed in Fields and Stemglanz (*Trends in Genetics* 10:286–292 (1994); which is incorporated herein by reference in its entirety). The methods used are briefly described below.

Complementary DNAs encoding proteins capable of interacting with the *Arabidopsis thaliana* D-type cyclins, D1 and D2, designated $CycD1_{At}$ and $CycD2_{At}$ were isolated using the two hybrid screen method essentially described by Fields and Song (*Nature* 340:245 (1989) and U.S. Pat. No. 5,283,173; which are incorporated by reference herein in their entirety and modified as described herein). The "bait" constructs contained an expression vector encoding a GAL4-CycD1$_{At}$ or Gal-4-CycD2$_{At}$ fusion protein. To construct the GAL4-CycD1$_{At}$ "bait" plasmid, pGBT9CycD1$_{At}$, the CycD1 insert from plasmid pJG8(D1) (Soni et al., *The Plant Cell* 7:85–103 (1995); which is incorporated herein by reference in its entirety) was obtained by PCR amplification with oligonucleotide primers designed to add a BamHI site to each end of the gene. The amplified PCR fragment encoding amino acids 1 of 334 of CycD1$_{At}$, encompassing the entire coding sequence, was digested with BamHI and ligated into the pGBT9 vector (Clontech Laboratories, Inc. and Bartel et al., in *Cellular Interaction in Development: A Practical Approach*, Ed. Hartley, Oxford University Press, Oxford, ENGLAND, pp. 153–179 (1993); which is incorporated herein by reference in its entirety) previously digested with BamHI to obtain a polynucleotide sequence encoding a GAL4-CycD1$_{At}$ fusion. Plasmid pGBT9 is a yeast 2 μM-bearing vector containing a GAL4 expression vector containing the *S. cerevisiae* ADH1 promoter, the GAL4 DNA binding domain a polylinker site and a terminator sequence containing a termination codon in all frames followed by the *S. cerevisiae* ADH1 terminator.

An *Arabidopsis thaliana* cDNA fusion library (Kim et al., *Proc. Natl. Acad. Sci. USA* 94:11786–11791 (1997); incorporated herein by reference) containing random-oligo-dT cDNA and the GAL4 activation domain was prepared as described by Kim et al., (supra). Briefly, total RNA was isolated from three-day old etiolated *Arabidopsis* by solubilization of embryos in guanidinium isothiocyanate followed by pelleting of the RNA through a cesium chloride gradient cushion.

First-strand cDNA was synthesized at 37° C. from 5 μg of poly(A) RNA with oligo(dT) and 1,000 Units of SUPERSCRIPT (BRL). After the second strand reaction, the cDNA was precipitated with spermine and washed with spermine wash buffer. The cDNA was dissolved in 40 μl of TE buffer and made flush with T4 DNA polymerase according to the suppliers instructions (New England Biolabs). After inactivation of the enzyme by the addition of 5 μl of 0.5 M EDTA, samples were extracted with phenol/chloroform and precipitated with ethanol. The cDNA was resuspended in 12 μl TE buffer and then ligated with 3 μl of equal mixture of phosphorylated adapters (100 μM) in a total volume of 20 μl at 4° C. overnight. The adapter sequences (Elledge et al., Proc. Natl. Acad. Sci. USA 88:1731–1735 (1991)) were annealed by heating for 2 min at 88° C., 10 min at 65° C., 10 min at 37° C., and 5 min at room temperature. After ligation, the samples were precipitated by the addition of spermine and washed as described (Elledge, supra).

The adapted cDNA was resuspended in 20 μl of TE and electrophoresed on a 1% low melting temperature agarose gel. cDNAs of more than 570 base pairs in length were gel-purified for ligation into λ-ACT arms. The cDNA prepared from 0.5 μg of poly(A) RNA was ligated to 2 μg of T-filled λ-ACT plasmid DNA in a volume of 5 μl at 4° C. overnight and packaged using GIGApack Gold packaging extract (Stratagene). Automatic subcloning conversion of the Arabidopsis cDNA library into the plasmid library was performed as described (Harper et al., Cell 75:805–816 (1993); incorporated herein by reference). The phage library was amplified in E. coli and stored at −80° C. in the presence of 7% dimethyl sulfoxide until used.

The two-hybrid screen was performed as described previously (Vojtek et al., Cell 74:205–214 (1993); and Hollenberg et al., Mol. Cell. Biol 15:3813–3822, (1995); each of which are incorporated by reference herein in their entirety) with some modifications. The S. cerevisiae strain Y190 (MATa, leu2-3,112, ura3-52, trp1-901, his3-200, ade2-101, GAL4-fal80, URA3 GAL-lacZ, LYS GAL-HIS3, cyh$^r$) was used as the host strain for the screen. The host strain was transformed with pGBT9cycD1$_{At}$ or pGBT9cycD2$_{At}$. The transformed host strain was subsequently transformed with the Arabidopsis fusion library. Transformants were selected in medium containing 3-amino-1,2,4-triazole (25 mM) and lacking histidine. The histidine-positive cells were assayed for β-galactosidase activity.

DNA isolated from transformed yeast exhibiting both vigorous growth on His$^-$ media and 3 aminotriazole containing media and also high levels of β-galactosidase activity was used to transform E. coli. Plasmid DNA from E. Coli was transformed back into yeast. From approximately 2×10$^6$ clones transformed with cyclin D1 as bait, three clones designated BRO2 (comprising the oligonucleotide sequence for BRO2, SEQ ID NO: 3), BRO3 (comprising the oligonucleotide sequence for BRO3, SEQ ID NO: 5), and BRO4 (comprising the oligonucleotide sequence for BRO4, SEQ ID NO: 7) were selected and sequenced by routine methods.

The amino acid sequence of each of the open reading frames containing a BRO gene was predicted from the determined nucleotide sequence of the clones. Examination of the open reading frame encoding BRO2 revealed a protein of approximately 128 amino acid residues with the initiating Met at residue 20 of SEQ ID NO: 4 and terminating with the Arg at amino acid residue 147. A similar examination of BRO3 revealed a protein of approximately 183 amino acid residues beginning with the Met at position 20 (SEQ ID NO: 6) and terminating with the Pro at residue position 202. Bro4 comprises an approximately 196 amino acid protein initiating at amino acid residue position 13 (SEQ ID NO: 8) and terminating with the Leu at position 208. Visual inspection of the amino acid sequences of BRO3 (SEQ ID NO: 6) and BRO4 (SEQ ID NO: 8) revealed a region of approximately 22 amino acids which were substantially homologous to the mammalian consensus cyclin-dependent kinase binding domain. Examination of the amino acid sequences of BRO2, BRO3 and BRO4 (SEQ ID NO: 4, SEQ ID NO: 6 and SEQ ID NO: 8 respectively) revealed a conserved region of about 6 amino acid residues approximately 17 to twenty amino acids upstream of the cdk binding domain. In mammalian cells it is well known that the cyclin binding domain is found at about this distance from the cdk binding domain. As all three clones were isolated based on binding to the plant D-like cyclin it was determined that this region of 6 amino acids is likely the cyclin binding domain. Therefore, BRO2, BRO3 and BRO4 were identified as cDNA fragments encoding cyclin binding proteins having the defined binding motif.

Approximately 7.2×10$^5$ clones transformed with cyclin D2 as bait were screened, one clone designated BRO1 (comprising the oligonucleotide sequence of BRO1, SEQ ID NO: 1) was selected for further analysis. The clone was sequenced and the amino acid sequence predicted from the DNA sequence of the clone (SEQ ID NO: 2). Examination of the amino acid sequence revealed a polypeptide of about 135 amino acid residues beginning with the Met at position 1 (SEQ ID NO: 2) and terminating with the Arg at position 135. Visual inspection of the putative amino acid sequence revealed an approximately seven amino acid sequence cyclin binding domain motif similar to that determined for BRO2, BRO3 and BRO4. The cDNA fragment of BRO1 was therefore identified as encoding a cyclin binding protein.

Initially it appeared from visual inspection of the amino acid sequences of BRO1 and BRO2 that the corresponding cDNA fragments might be incomplete. The remainder of the open reading frame which encodes the complete gene for these proteins was be determined by probing an Arabidopsis hypocotyl genomic library in a λ vector. The library was probed for the BRO2 and BRO1 genes and the complete sequences are as provided herein. Only the sequence for BRO1 was determined to have been incomplete.

EXAMPLE 2

In this example each of the nucleic acid sequences identified to encode a cyclin dependent protein kinase inhibitor has been cloned from the pACT vector used in the yeast two hybrid screen, inserted into a pCGN1547 plasmid in the reverse orientation and used to transform Arabidopsis plants. The plants transgenic for antisense molecules to the BRO genes are examined for phenotypic changes characteristic of modulation of cell cycle regulation, including, i.e., rate of root, leaf and stem growth, increase in biomass production, and the like.

Briefly, the nucleotide sequences encoding BRO family proteins were cloned from the pACT vectors into the plasmid pLAY112 which contains a chimeric plant promoter comprising combined CaMV 35S and MAS elements. (Comai et al., Plant Mol. Biol. 15:373–381 (1990), which is incorporated herein in its entirety) BRO1 and BRO2 were both digested with BglII and then cloned into the BamHI site of pLAY112. BRO3 was cut with XhoI and the ends were filled with Klenow fragment. The XhoI fragment containing the BRO3 encoding sequence was ligated into pLAY112 previously digested with SmaI. BRO4 was digested with HincII (blunt) and EcoRI. The EcoRI ends were filled with dNTPs and Klenow. The BRO4 fragment was isolated and ligated into pLAY112 previously digested with SmaI. The ligation mixtures were transformed into *E. coli* and transformants were selected on the appropriate media. Selected transformants were grown in liquid LB media with antibiotics. Plasmid DNA was isolated from each transformant and the DNA was tested for the appropriate insert.

Plasmids pLAY112BRO1, pLAY112BRO3 and pLAY112BRO4 were cut with PstI and cloned into the PstI site of plasmid pCGN1547 (McBride et al., *Plant Mol. Biol.* 14:269–276 (1990)). Plasmid pLAY112BRO2 was cut with BglII and cloned into the BamHI site of pCGN1547. The ligation mixtures were transformed into *E. coli* and transformants were selected on the appropriate media. Selected transformants were grown in liquid media with antibiotics. Plasmid DNA was isolated from each transformant and the DNA was tested for the appropriate insert.

The pCGN1547BRO and pCGN1547BRO2 plasmids were used to transform *Agrobacterium tumefaciens*. *Arabidopsis thaliana* was transformed with each BRO family member by vacuum infiltration (Bechtold et al., *Acad. Sci. Paris, Life Sci.* 316:1194 (1993)), and transgenic seedlings (TO generation) were selected on AB plates with 50 µg/ml kanimycin and compared to wild-type.

EXAMPLE 3

In this example the effect of suppression of plant D-like cyclin inhibitor genes on cellular proliferation was examined.

Briefly, genes were engineered that contained "inverted repeats" of ICK1 (stem of 244 bp, loop of 420 bp) and BRO4 (stem of 203 bp and loop of 303 bp) coding regions (Waterhouse et al., *Proc. Natl. Acad. Sci USA* 95:13959–135964 (1998)). To construct the ICK1- and BRO4-Inverted Repeats the target fragments were amplified by PCR using the primers shown in Table 1. Each primer contains an appropriate restriction site that can be cut to allow the assembly of the individual PCR products into the inverted repeat.

TABLE 1

PCR Primers used to construct inverted repeats structures.

| | | |
|---|---|---|
| ICK1 IR1 | ggtacccgatttcgagaaggagaagc | SEQ ID NO:11 |
| ICK1 IR2 | gatatcgacacgacttttctgggctc | SEQ ID NO:12 |
| ICK1 IR3 | gatatcctacggagccggagaattg | SEQ ID NO:13 |
| ICK1 IR4 | actagtttgtttctcagcttccacaaaa | SEQ ID NO:14 |
| ICK1 IR5 | actagtgacacgacttttctgggctc | SEQ ID NO:15 |
| ICK1 IR6 | gagctccgatttcgagaaggagaagc | SEQ ID NO:16 |
| BRO4 IR1 | ggtacccgacaacagaaatggaatcatc | SEQ ID NO:17 |
| BRO4 IR2 | gtcgacaaagtcgatcccacttgtagc | SEQ ID NO:18 |
| BRO4 IR3 | gtcgacaaagcgagagcttgcagaag | SEQ ID NO:19 |
| BRO4 IR4 | actagtcggtttcgatttgatgatcc | SEQ ID NO:20 |
| BRO4 IR5 | actagtaaagtcgatcccacttgtagc | SEQ ID NO:21 |
| BRO4 IR6 | gagctccgacaacagaaatggaatcatc | SEQ ID NO:22 |

The constructions were spliced into pLAY 112, a plasmid that combines the elements of CaMV 35S and the mannopine synthase 3' region to form the hybrid promoter Mac (Comai et al., *Plant Mol. Biol.* 15:373–381 (1990)), and introduced into the binary vector pCGN1547 (McBride and Summerfelt, *Plant Mol. Biol.* 14:269–276 (1990)) using standard methods. The binary vector was transformed into *Agrobacterium tumefaciens* strain At503. The genes were transformed into *Arabidopsis* ecotype Ler and Col-0 (Bechtold and Pelletier, *Methods Mol. Biol.* 82:259–266 (1998)). Transgenic plants were identified by their kanamycin resistance phenotype and examined for their morphological phenotype.

ICK1-IR Phenotype

Figure 2:
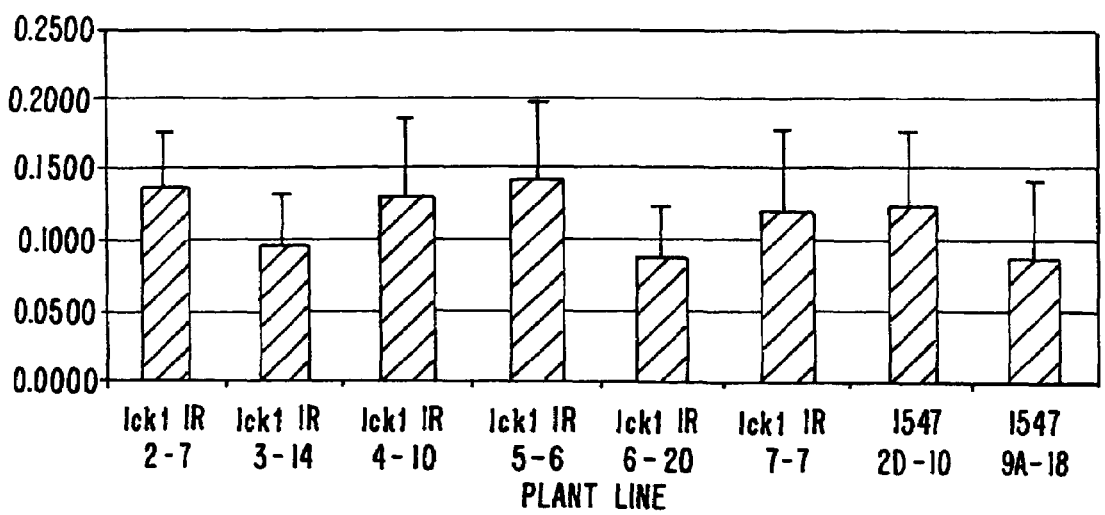
FIG. 2 depicts measurement of the weight of the first cauline leaf of several ICK-IR transgenic plant lines and control plants.
Figure 3:
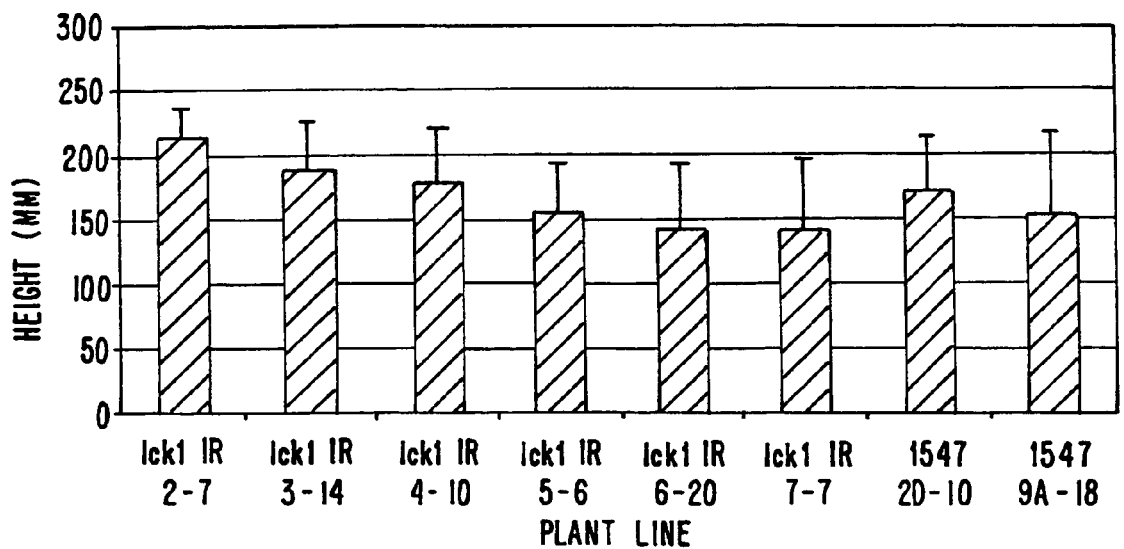
FIG. 3 depicts measurement of the stem heights (mm) of various ICK-IR transgenic plant lines and control plants.

The plants transgenic for ICK-IR demonstrated three signs of increased growth: larger and wider leaves (both cauline and rosette), 3 to 4 carpels instead of 2, and cracks in the main stem, as if the inner stem tissues grew excessively and were not matched by growth in the outside tissue layers. Measurements of leaf and carpel sizes and numbers of various transgenic plant lines and control plants are depicted in FIGS. 1 through 3 and Table 2. The phenotype has been measured in two different experiments.

The phenotype of multiple carpels is particularly important in interpreting the effects of ICK1 suppression. This phenotype has been well studied because it is similar to that caused by mutations of the CLA VATA 1, 2, and 3 genes (Chen et al., *Genesis* 26:42–54 (2000); Clark et al., *Development* 122:1567–1575 (1996); Fletcher et al., *Science* 283:1911–1914 (1999)).

TABLE 2

Carpel Number ICK1-IR and control (1547 plants)

| | Siliques (carpel #)[1] | |
|---|---|---|
| Genotype | 2 | 3 or 4 |
| Ick 1 IR 2-7 | 31 | 1 |
| Ick 1 IR 3-14 | 32 | 4 |
| Ick 1 IR 4-10 | 8 | 9 |
| Ick 1 IR 5-6 | 25 | 1 |
| Ick 1 IR 6-20 | 7 | 14 |
| Ick 1 IR 7-7 | 5 | 14 |
| 1547 2D 10 | 18 | |
| 1547 9A 18 | 16 | |

[1]The first four siliques produced were examined

Meristems are the apical organs responsible for shoot and root growth. In clavata mutants excessive cell divisions form larger meristems, which in turn form supernumerary carpels. CLAVATA genes encode the components of a cell-to-cell communication system. The ICK1-IR phenotype is the first direct evidence that larger meristems can be formed by controlling regulators of cell divisions. This provides evidence that ICK1 manipulations can be used to modify the growth properties of plants.

BRO4 Phenotype

Figure 4:
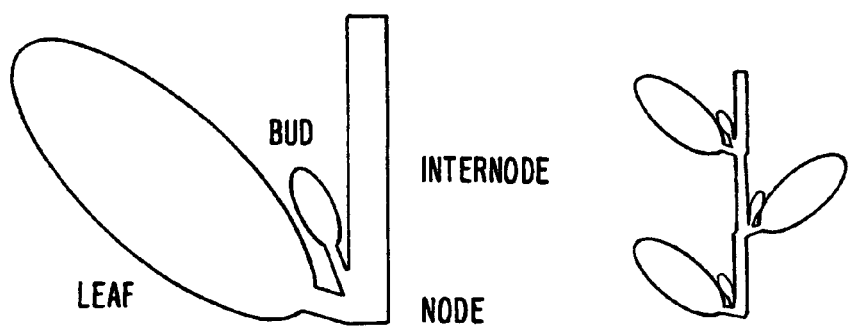
FIG. 4 is a pictorial representation of a metamer unit and structure in a plant.

Plants transgenic for BRO4-IR were bushier, i.e., they had more coflorescences and more leaves on each coflorescence. The plants appear to have developed this phenotype by having formed more metamers, the basic units of development. Each metamer consists of an internode and an organ-bearing node (FIG. 4). Metamers are formed by the action of the apical meristem. Each lateral outgrowth (organ primordia) on the meristem apex forms a node. Each node bears a leaf and in the axil of the leaf there is a lateral shoot. Therefore, a plant with more nodes becomes bushier by forming more lateral shoots. It is possible that BRO4 suppression results in accelerated formation of lateral organs, and therefore, more nodes.

Deposit of Biological Material

The following materials have been deposited with the American Type Culture Collection, 10801 University Boulevard, Manassas, Va. 20110-2209, under the terms of the Budapest Treaty.

| Plasmid | Accession No. | Deposit Date |
|---|---|---|
| pACT BRO1 | ATCC 203953 | Apr. 23, 1999 |
| pACT BRO2 | ATCC 203954 | Apr. 23, 1999 |
| pACT BRO3 | ATCC 203955 | Apr. 23, 1999 |
| pACT BRO4 | ATCC 203956 | Apr. 23, 1999 |

Although the foregoing invention has been described in some detail by way of illustration and example for purposes of clarity of understanding, it will be obvious that certain changes and modifications may be practiced within the scope of the appended claims.

What is claimed is:

1. An isolated nucleotide sequence which encodes the plant D-like cyclin inhibitor protein designated BRO4 as depicted in SEQ ID NO: 8 initiating at amino acid residue position 13 and terminating at amino acid residue position 208.

2. The isolated nucleotide sequence of claim 1, wherein the nucleotide sequence is that depicted in SEQ ID NO: 7.

3. A vector comprising the nucleotide sequence of claim 1.

4. The vector according to claim 3, wherein the vector further comprises a selectable marker.

5. The vector according to claim 3, wherein the vector further comprises an operably linked promoter that functions in a plant cell.

6. The vector according to claim 5, wherein the promoter is associated with the gene encoding CaMV 35S, tomato E8, patatin, ubiquitin, mannopine synthase, rice actin I, soybean seed protein glycinin (Gly1), soybean vegetative storage protein, or is the hybrid promoter MAC comprising elements of the promoter associated with the gene encoding CaMV 35S and the 3' region of the gene encoding mannopine synthase.

7. A host cell comprising the vector of claim 3.

8. A host cell comprising the vector of claim 4.

9. A host cell comprising the vector of claim 5.

10. A host cell comprising the vector of claim 6.

* * * * *

UNITED STATES PATENT AND TRADEMARK OFFICE
CERTIFICATE OF CORRECTION

| | | |
|---|---|---|
| PATENT NO. | : 7,230,089 B1 | Page 1 of 1 |
| APPLICATION NO. | : 09/980758 | |
| DATED | : June 12, 2007 | |
| INVENTOR(S) | : James M. Roberts and Beth L. Kelly | |

It is certified that error appears in the above-identified patent and that said Letters Patent is hereby corrected as shown below:

Column 1, line 18, please delete, "The U.S. government may have certain rights in the invention pursuant to Grant No. R01 CA67893 received from the U.S. National Institutes of Health."

and insert

-- This invention was made with government support under R01 CA67893 awarded by U.S. National Institutes of Health. The government has certain rights in the invention. --

Signed and Sealed this

Seventeenth Day of March, 2009

JOHN DOLL
*Acting Director of the United States Patent and Trademark Office*

SEQUENCE LISTING

<160> NUMBER OF SEQ ID NOS: 22

<210> SEQ ID NO 1
<211> LENGTH: 408
<212> TYPE: DNA
<213> ORGANISM: Arabidopsis thaliana

<400> SEQUENCE: 1

```
atggcatcaa aaaagcaag aaaccaaac cgagccgaaa agaaactcac aagaagctgt      60
ttcaagaaac aagttcctca acacaacaac atcaacacaa gtataactct cgatcaaaca    120
tctacatcta ctattgtctc tacatgttct tcttcatcaa cgactttgtc ttctcctcta    180
gacacaatct actctgttcc ctctccatcc ccagcagcgg tgctgacgtc accaggcggt    240
tgttgtaccc cgaaagccaa gaagtctagg ataccggaga tgctgacgtg tccaccggcg    300
ccgaagaagc aaagggtctc gaaaaactgt gtgttacgac ggagacagat cgttttcttt    360
gctccgccgg agatagagct cttcttcgtc aacgcacacg atcgatga                 408
```

<210> SEQ ID NO 2
<211> LENGTH: 135
<212> TYPE: PRT
<213> ORGANISM: Arabidopsis thaliana

<400> SEQUENCE: 2

```
Met Ala Ser Lys Lys Ala Arg Lys Pro Asn Arg Ala Glu Lys Lys Leu
1               5                   10                  15

Thr Arg Ser Cys Phe Lys Lys Gln Val Pro Gln His Asn Asn Ile Asn
            20                  25                  30

Thr Ser Ile Thr Leu Asp Gln Thr Ser Thr Ser Thr Ile Val Ser Thr
        35                  40                  45

Cys Ser Ser Ser Thr Thr Leu Ser Ser Pro Leu Asp Thr Ile Tyr
    50                  55                  60

Ser Val Pro Ser Pro Ser Pro Ala Ala Val Leu Thr Ser Pro Gly Gly
65                  70                  75                  80

Cys Cys Thr Pro Lys Ala Lys Lys Ser Arg Ile Pro Glu Met Leu Thr
                85                  90                  95

Cys Pro Pro Ala Pro Lys Lys Gln Arg Val Ser Lys Asn Cys Val Leu
            100                 105                 110

Arg Arg Arg Gln Ile Val Phe Phe Ala Pro Pro Glu Ile Glu Leu Phe
        115                 120                 125

Phe Val Asn Ala His Asp Arg
    130                 135
```

<210> SEQ ID NO 3
<211> LENGTH: 639
<212> TYPE: DNA
<213> ORGANISM: Arabidopsis thaliana

<400> SEQUENCE: 3

```
ctcgagattt accaaaaaag tttcccaaaa aaacaaaaac atacacaagt ttagatatgg      60
atcttgaatt actacaagat ttgtccaaat tcaatttccc aacacccatc aagatccgat     120
ccaaaacctc aaaaacaaag aaggacgaag gtgatgacga cgaagatgac ctccgctgca     180
gcacacccac atcccaagaa cacaagattc ccgccgtcgt agactctcca cctcctccgc     240
cgagaaaacc ccggccacca ccgtcagcac cgtcggctac ggcggctctg atgatcagat     300
cgtgcaagag gaagcttta gtgtcgactt gtgagataat catgaatcgg aagagattg      360 accgtttctt ctcctccgtc tacaatgaga cgtcgactac ggctaaacgg cggagaagtt     420
acccttattg ttctcgaaga tgaggcttaa ttcaatattt acatttttt acagttttac      480 tggaaatatt gtgaaattaa ttatctgttg gtgttcggtt ttaaatattt ttaatttaat     540
tatgaatatg gatggataat tttctgcaac cgcgcatatt aatttcgcat ggaggggtcg     600
atgttgtaaa ttgagtaata aatgaaggta aatctcgag                            639
```

<210> SEQ ID NO 4
<211> LENGTH: 213
<212> TYPE: PRT
<213> ORGANISM: Arabidopsis thaliana
<220> FEATURE:
<221> NAME/KEY: MISC_FEATURE
<222> LOCATION: (148)..(148)
<223> OTHER INFORMATION: Xaa = any amino acid
<220> FEATURE:
<221> NAME/KEY: MISC_FEATURE
<222> LOCATION: (165)..(165)
<223> OTHER INFORMATION: Xaa = any amino acid
<220> FEATURE:
<221> NAME/KEY: MISC_FEATURE
<222> LOCATION: (167)..(167)
<223> OTHER INFORMATION: Xaa = any amino acid
<220> FEATURE:
<221> NAME/KEY: MISC_FEATURE
<222> LOCATION: (175)..(175)
<223> OTHER INFORMATION: Xaa = any amino acid
<220> FEATURE:
<221> NAME/KEY: MISC_FEATURE
<222> LOCATION: (182)..(182)
<223> OTHER INFORMATION: Xaa = any amino acid
<220> FEATURE:
<221> NAME/KEY: MISC_FEATURE
<222> LOCATION: (205)..(205)
<223> OTHER INFORMATION: Xaa = any amino acid

<400> SEQUENCE: 4

```
Pro Arg Asp Leu Pro Lys Lys Phe Pro Lys Lys Thr Lys Thr Tyr Thr
1               5                   10                  15

Ser Leu Asp Met Asp Leu Glu Leu Leu Gln Asp Leu Ser Lys Phe Asn
            20                  25                  30

Phe Pro Thr Pro Ile Lys Ile Arg Ser Lys Thr Ser Lys Thr Lys Lys
        35                  40                  45

Asp Glu Gly Asp Asp Asp Glu Asp Asp Leu Arg Cys Ser Thr Pro Thr
    50                  55                  60

Ser Gln Glu His Lys Ile Pro Ala Val Val Asp Ser Pro Pro Pro
65                  70                  75                  80

Pro Arg Lys Pro Arg Pro Pro Ser Ala Pro Ser Ala Thr Ala Ala
```

```
                85                  90                  95
Leu Met Ile Arg Ser Cys Lys Arg Lys Leu Leu Val Ser Thr Cys Glu
            100                 105                 110

Ile Ile Met Asn Arg Glu Glu Ile Asp Arg Phe Phe Ser Ser Val Tyr
            115                 120                 125

Asn Glu Thr Ser Thr Thr Ala Lys Arg Arg Ser Tyr Pro Tyr Cys
        130                 135                 140

Ser Arg Arg Xaa Gly Leu Ile Gln Tyr Leu His Phe Phe Thr Val Leu
145                 150                 155                 160

Leu Glu Ile Leu Xaa Asn Xaa Leu Ser Val Gly Val Arg Phe Xaa Ile
                165                 170                 175

Phe Leu Ile Glx Leu Xaa Ile Trp Met Asp Asn Phe Leu Gln Pro Arg
            180                 185                 190

Ile Leu Ile Ser His Gly Gly Val Asp Val Val Asn Xaa Val Ile Asn
            195                 200                 205

Glu Gly Lys Ser Arg
        210

<210> SEQ ID NO 5
<211> LENGTH: 809
<212> TYPE: DNA
<213> ORGANISM: Arabidopsis thaliana

<400> SEQUENCE: 5
ctcgagattt accacgagat gtggttgaag agaatggagt tacgacgacg acggtgaaac        60
gaaggaagat ggaggaggaa gtggatttag tggaatctag gataattctg tctccgtgtg       120
tacaggcgac gaatcgcggt ggaattgtgg cgagaaattc agcaggagcg tcggagacga       180
gtgttgttat agtacgacgg cgagattctc ctccggttga agaacagtgt caaatcgaag       240
aagaagattc gtcggtttcg tgttgttcta catcggaaga gaaatcgaaa cggagaatcg       300
aatttgtaga tcttgaggaa ataacggtg acgatcgtga acagaaacg tcgtggatt        360 acgatgattt gaataagagt gaggaatcga tgaacatgga ttcttcttcg gtggctgttg       420
aagatgtaga gtctcgccgc aggttaagga agagtctcca tgagacggtg aaggaagctg       480
agttagaaga ctttttcag gtggcggaga agatcttcg gaataagttg ttggaatgtt        540
ctatgaagta taacttcgat ttcgagaaag atgagccact tggtggagga agatacgagt       600
gggttaaatt gaatccatga agaagacgat gatgataatg atgatcattg ttttcaccaa       660
agtacttatt atttctcttc tgtaataatc tttgctttga ttttctttt aacaaaatcc        720 aaatgtagat atctttctct cgaataatca ataacatgta attcaactaa aaaaaaaaa        780 aaaaaaaaa aaaaaggta aatctcgag                                           809

<210> SEQ ID NO 6
<211> LENGTH: 203
<212> TYPE: PRT
<213> ORGANISM: Arabidopsis thaliana
<220> FEATURE:
<221> NAME/KEY: MISC_FEATURE
<222> LOCATION: (203)..(203)
<223> OTHER INFORMATION: Xaa = any amino acid

<400> SEQUENCE: 6

Pro Arg Asp Val Val Glu Glu Asn Gly Val Thr Thr Thr Val Lys
1               5                   10                  15

Arg Arg Lys Met Glu Glu Glu Val Asp Leu Val Glu Ser Arg Ile Ile
            20                  25                  30
```

```
Leu Ser Pro Cys Val Gln Ala Thr Asn Arg Gly Gly Ile Val Ala Arg
            35                  40                  45

Asn Ser Ala Gly Ala Ser Glu Thr Ser Val Val Ile Val Arg Arg Arg
 50                  55                  60

Asp Ser Pro Val Glu Glu Gln Cys Gln Ile Glu Glu Glu Asp Ser
65                  70                  75                  80

Ser Val Ser Cys Cys Ser Thr Ser Glu Glu Lys Ser Lys Arg Arg Ile
                85                  90                  95

Glu Phe Val Asp Leu Glu Glu Asn Asn Gly Asp Asp Arg Glu Thr Glu
            100                 105                 110

Thr Ser Trp Ile Tyr Asp Asp Leu Asn Lys Ser Glu Glu Ser Met Asn
            115                 120                 125

Met Asp Ser Ser Val Ala Val Glu Asp Val Glu Ser Arg Arg Arg
    130                 135                 140

Leu Arg Lys Ser Leu His Glu Thr Val Lys Glu Ala Glu Leu Glu Asp
145                 150                 155                 160

Phe Phe Gln Val Ala Glu Lys Asp Leu Arg Asn Lys Leu Leu Glu Cys
                165                 170                 175

Ser Met Lys Tyr Asn Phe Asp Phe Glu Lys Asp Glu Pro Leu Gly Gly
            180                 185                 190

Gly Arg Tyr Glu Trp Val Lys Leu Asn Pro Xaa
            195                 200
```

```
<210> SEQ ID NO 7
<211> LENGTH: 626
<212> TYPE: DNA
<213> ORGANISM: Arabidopsis thaliana

<400> SEQUENCE: 7
ctcgagattt acccaaaaat ccaagagaga aaaaatgag cgagagaaag cgagagcttg      60
cagaagaagc ttcaagcaca agcttctcac cactgaagaa aacgaagctt aatgattctt     120
ctgattcatc accggactct catgacgtca tcgtcttcgc ggtttcatct tcttccgttg    180
cttcgtcggc ggctttagcg tctgatgaat gttccgttac catcggtgga agaagaagtg     240
atcagtcctc gagtatcagc tccggttgtt tcaccagtga atcgaaagaa atcgcgaaga     300
acagttcgtc gtttggtgta gatctggagg atcatcaaat cgaaaccgaa accgaaacct    360
caacattcat caccagcaat ttcagaaaag agacgagtcc agtgagtgag ggtttgggag    420
aaacgacaac agaaatggaa tcatcatcgg caacgaagag aaaacaaccg ggggtgagga    480
agactccaac ggcggcggag attgaggatt tgttctcgga gctagagagt ccagacgata    540
agaagaagca attcatagaa aagtacaact tcgatattgt caatgacgaa ccgcttgaag    600
gtcgctacaa gtgggatcga ctttaa                                          626

<210> SEQ ID NO 8
<211> LENGTH: 209
<212> TYPE: PRT
<213> ORGANISM: Arabidopsis thaliana
<220> FEATURE:
<221> NAME/KEY: MISC_FEATURE
<222> LOCATION: (209)..(209)
<223> OTHER INFORMATION: Xaa = any amino acid

<400> SEQUENCE: 8

Pro Arg Asp Leu Pro Lys Asn Pro Arg Glu Lys Lys Met Ser Glu Arg
1               5                   10                  15
```

```
Lys Arg Glu Leu Ala Glu Ala Ser Ser Thr Ser Phe Ser Pro Leu
             20                  25                  30

Lys Lys Thr Lys Leu Asn Asp Ser Ser Asp Ser Ser Pro Asp Ser His
         35                  40                  45

Asp Val Ile Val Phe Ala Val Ser Ser Ser Val Ala Ser Ser Ala
 50                  55                  60

Ala Leu Ala Ser Asp Glu Cys Ser Val Thr Ile Gly Gly Glu Glu Ser
 65                  70                  75                  80

Asp Gln Ser Ser Ser Ile Ser Ser Gly Cys Phe Thr Ser Glu Ser Lys
                 85                  90                  95

Glu Ile Ala Lys Asn Ser Ser Ser Phe Gly Val Asp Leu Glu Asp His
             100                 105                 110

Gln Ile Glu Thr Glu Thr Glu Thr Ser Thr Phe Ile Thr Ser Asn Phe
            115                 120                 125

Arg Lys Glu Thr Ser Pro Val Ser Glu Gly Leu Gly Glu Thr Thr Thr
        130                 135                 140

Glu Met Glu Ser Ser Ser Ala Thr Lys Arg Lys Gln Pro Gly Val Arg
145                 150                 155                 160

Lys Thr Pro Thr Ala Ala Glu Ile Glu Asp Leu Phe Ser Glu Leu Glu
                165                 170                 175

Ser Pro Asp Asp Lys Lys Lys Gln Phe Ile Glu Lys Tyr Asn Phe Asp
            180                 185                 190

Ile Val Asn Asp Glu Pro Leu Glu Gly Arg Tyr Lys Trp Asp Arg Leu
        195                 200                 205

Xaa

<210> SEQ ID NO 9
<211> LENGTH: 6
<212> TYPE: PRT
<213> ORGANISM: Arabidopsis thaliana
<220> FEATURE:
<221> NAME/KEY: MISC_FEATURE
<222> LOCATION: (2)..(2)
<223> OTHER INFORMATION: Xaa = Leu, Ile or another hydrophobic amino
      acid
<220> FEATURE:
<221> NAME/KEY: MISC_FEATURE
<222> LOCATION: (3)..(3)
<223> OTHER INFORMATION: Xaa = Glu or Asp
<220> FEATURE:
<221> NAME/KEY: MISC_FEATURE
<222> LOCATION: (4)..(4)
<223> OTHER INFORMATION: Xaa = Leu, Arg, Asp or any other amino acid
      residue
<220> FEATURE:
<221> NAME/KEY: MISC_FEATURE
<222> LOCATION: (5)..(5)
<223> OTHER INFORMATION: Xaa = Phe, Leu or another hydrophobic amino
      acid residue

<400> SEQUENCE: 9

Glu Xaa Xaa Xaa Xaa Phe
 1               5

<210> SEQ ID NO 10
<211> LENGTH: 23
<212> TYPE: PRT
<213> ORGANISM: Arabidopsis thaliana
<220> FEATURE:
<221> NAME/KEY: MISC_FEATURE
<222> LOCATION: (6)..(6)
<223> OTHER INFORMATION: Xaa = Phe or Ile
<220> FEATURE:
<221> NAME/KEY: MISC_FEATURE
```

```
<222> LOCATION: (7)..(7)
<223> OTHER INFORMATION: Xaa = Glu or Val
<220> FEATURE:
<221> NAME/KEY: MISC_FEATURE
<222> LOCATION: (8)..(8)
<223> OTHER INFORMATION: Xaa = Lys or Asn
<220> FEATURE:
<221> NAME/KEY: MISC_FEATURE
<222> LOCATION: (9)..(9)
<223> OTHER INFORMATION: Xaa = Asp or Glu
<220> FEATURE:
<221> NAME/KEY: MISC_FEATURE
<222> LOCATION: (10)..(10)
<223> OTHER INFORMATION: Xaa = Glu or Lys
<220> FEATURE:
<221> NAME/KEY: MISC_FEATURE
<222> LOCATION: (13)..(13)
<223> OTHER INFORMATION: Xaa = Gly or Glu
<220> FEATURE:
<221> NAME/KEY: MISC_FEATURE
<222> LOCATION: (14)..(14)
<223> OTHER INFORMATION: Xaa = Absent or Gly
<220> FEATURE:
<221> NAME/KEY: MISC_FEATURE
<222> LOCATION: (18)..(18)
<223> OTHER INFORMATION: Xaa = Glu or Lys
<220> FEATURE:
<221> NAME/KEY: MISC_FEATURE
<222> LOCATION: (20)..(20)
<223> OTHER INFORMATION: Xaa = Val or Asp
<220> FEATURE:
<221> NAME/KEY: MISC_FEATURE
<222> LOCATION: (21)..(21)
<223> OTHER INFORMATION: Xaa = Lys or Arg
<220> FEATURE:
<221> NAME/KEY: MISC_FEATURE
<222> LOCATION: (23)..(23)
<223> OTHER INFORMATION: Xaa = Asn or Glu

<400> SEQUENCE: 10

Lys Tyr Asn Phe Asp Xaa Xaa Xaa Xaa Xaa Pro Leu Xaa Xaa Gly Arg
1               5                   10                  15

Tyr Xaa Trp Xaa Xaa Leu Xaa
            20

<210> SEQ ID NO 11
<211> LENGTH: 26
<212> TYPE: DNA
<213> ORGANISM: Artificial Sequence
<220> FEATURE:
<223> OTHER INFORMATION: PCR Primer

<400> SEQUENCE: 11
ggtacccgat tcgagaagg agaagc                                    26

<210> SEQ ID NO 12
<211> LENGTH: 26
<212> TYPE: DNA
<213> ORGANISM: Artificial Sequence
<220> FEATURE:
<223> OTHER INFORMATION: PCR Primer

<400> SEQUENCE: 12
gatatcgaca cgactttct gggctc                                    26

<210> SEQ ID NO 13
<211> LENGTH: 25
<212> TYPE: DNA
<213> ORGANISM: Artificial Sequence
<220> FEATURE:
<223> OTHER INFORMATION: PCR Primer
```

<400> SEQUENCE: 13
gatatcctac ggagccggag aattg                                          25

<210> SEQ ID NO 14
<211> LENGTH: 28
<212> TYPE: DNA
<213> ORGANISM: Artificial Sequence
<220> FEATURE:
<223> OTHER INFORMATION: PCR Primer

<400> SEQUENCE: 14
actagtttgt ttctcagctt ccacaaaa                                       28

<210> SEQ ID NO 15
<211> LENGTH: 26
<212> TYPE: DNA
<213> ORGANISM: Artificial Sequence
<220> FEATURE:
<223> OTHER INFORMATION: PCR Primer

<400> SEQUENCE: 15
ggtacccgat ttcgagaagg agaagc                                         26

<210> SEQ ID NO 16
<211> LENGTH: 26
<212> TYPE: DNA
<213> ORGANISM: Artificial Sequence
<220> FEATURE:
<223> OTHER INFORMATION: PCR Primer

<400> SEQUENCE: 16
actagtgaca cgactttct gggctc                                          26

<210> SEQ ID NO 17
<211> LENGTH: 28
<212> TYPE: DNA
<213> ORGANISM: Artificial Sequence
<220> FEATURE:
<223> OTHER INFORMATION: PCR Primer

<400> SEQUENCE: 17
ggtacccgac aacagaaatg gaatcatc                                       28

<210> SEQ ID NO 18
<211> LENGTH: 27
<212> TYPE: DNA
<213> ORGANISM: Artificial Sequence
<220> FEATURE:
<223> OTHER INFORMATION: PCR Primer

<400> SEQUENCE: 18
gtcgacaaag tcgatcccac ttgtagc                                        27

<210> SEQ ID NO 19
<211> LENGTH: 26
<212> TYPE: DNA
<213> ORGANISM: Artificial Sequence
<220> FEATURE:
<223> OTHER INFORMATION: PCR Primer

<400> SEQUENCE: 19
gtcgacaaag cgagagcttg cagaag                                         26

<210> SEQ ID NO 20
<211> LENGTH: 26

-continued

```
<212> TYPE: DNA
<213> ORGANISM: Artificial Sequence
<220> FEATURE:
<223> OTHER INFORMATION: PCR Primer

<400> SEQUENCE: 20
actagtcggt ttcgatttga tgatcc                                      26

<210> SEQ ID NO 21
<211> LENGTH: 27
<212> TYPE: DNA
<213> ORGANISM: Artificial Sequence
<220> FEATURE:
<223> OTHER INFORMATION: PCR Primer

<400> SEQUENCE: 21
actagtaaag tcgatcccac ttgtagc                                     27

<210> SEQ ID NO 22
<211> LENGTH: 28
<212> TYPE: DNA
<213> ORGANISM: Artificial Sequence
<220> FEATURE:
<223> OTHER INFORMATION: PCR Primer

<400> SEQUENCE: 22
gagctccgac aacagaaatg gaatcatc                                    28
```